United States Patent [19]

Collins et al.

[11] Patent Number: 5,126,322

[45] Date of Patent: Jun. 30, 1992

[54] PANCREATIC SECRETORY TRYSPIN INHIBITOR AND VARIANTS THEREOF PRODUCED BY A RECOMBINANT HOST THEREFORE AND PHARMACEUTICAL USE THEREOF

[75] Inventors: John Collins; Helmut Blöcker, both of Braunschweig; Ronald Frank, Wolfenbuettel; Friedhelm Maywald, Braunschweig; Hans Fritz, Hohenbrunn; Wolfgang Bruns, Wuppertal, all of Fed. Rep. of Germany

[73] Assignee: Bayer Aktiengesellschaft, Leverkusen, Fed. Rep. of Germany

[21] Appl. No.: 685,798

[22] Filed: Apr. 16, 1991

Related U.S. Application Data

[63] Continuation of Ser. No. 134,724, Dec. 18, 1987, abandoned.

[30] Foreign Application Priority Data

Jan. 7, 1987 [GB] United Kingdom ............... 8700204

[51] Int. Cl.⁵ .................. A61K 37/02; C07K 7/10; C07K 7/64
[52] U.S. Cl. .......................... 514/12; 514/9; 514/2; 930/250; 930/260; 930/270; 530/324; 530/325; 530/350; 435/69.2; 435/69.1
[58] Field of Search ............ 530/324, 325, 350, 317; 514/12, 2, 9; 435/69.2, 69.1; 930/250, 260, 270

[56] References Cited

U.S. PATENT DOCUMENTS 4,282,318  8/1981  Oeding et al. ............... 530/324
4,760,130  7/1988  Thompson et al. .......... 530/350

FOREIGN PATENT DOCUMENTS 0264118   4/1988  European Pat. Off.
WO86/03519 6/1986 PCT Int'l Appl.
WO88/03171 5/1988 PCT Int'l Appl.

OTHER PUBLICATIONS

Kingston et al., Biochem. J. (1986), vol. 233, pp. 443–450.
Izumoto et al., Gene, vol. 59, 1987, pp. 151-159.
Chem. Abs., vol. 103, No. 19, 156 304h, 1985, Kikuchi et al.
Tomatic et al., Chem. Abs., vol. 92, No. 17, 147198d, 1979.
Greene et al., Chem. Abs., vol. 83, No. 1, 3642k, 1974.
Boeldicke et al., Chem. Abs., vol. 109, No. 17, 1476012, 1988.
Methods Enzymol., 45, 813-825.
T. M. Aniatis et al., Molecular Cloning: A Laboratory Manual, 1982, Cold Spring Harbor Laboratory.
J. Biochemistry, Band 98, No. 3, Jun. 1985, Sieten 687–694; N. Kikuchi et al., "The Multiplicity of Human Pancreatic Secretory Trypsin Inhibitor".
Biochemical and Biophysical Research Communications, Band 132, Nr. 2, 30., Oct. 1985, Seiten 605–612, Academic Press, Inc.; T. Yamamoto et al., "Molecular Cloning and Nucleotide Sequence of Human Pancreatic Secretory Trypsin Inhibitor (PSTI) cDNA".

(List continued on next page.)

Primary Examiner—Lester L. Lee
Assistant Examiner—T. Wessendorf
Attorney, Agent, or Firm—Sprung Horn Kramer & Woods

[57] ABSTRACT

The present invention relates to a peptide having essentially the amino acid sequence of pancreatic secretory trypsin inhibitor (PSTI). The present invention also relates to variants of such peptide wherein one or more of the amino acids in the original sequence are replaced by other amino acids. These peptides show an advantageously modified specificity in their inhibitory action. A method of preparation of the peptides and their pharmaceutical use is also described.

4 Claims, 8 Drawing Sheets

OTHER PUBLICATIONS

The Embo Journal, Band 5, Nr. 12, 1986, Seiten 3219-3225, IRL Press Ltd., Oxford, GB; B. Von Wilcken-Bergmann et al.: "A Synthetic Operon Containing 14 Bovine Pancreatic Trypsin Inhibitor Genes is Express in *E. coli*".

Journal of Biological Chemistry, Band 261, Nr. 16, Jun. 5, 1986, Seiten 7115-7118, The American Society of Biological Chemists, Inc., US: C. B. Marks et al: "Production of Native, Correctly Folded Bovine Pancreatic Trypsin Inhibitor by *Escherichia coli*".

Chemical Abstracts, Band 96, 1982, Seite 338, Zusammenfassung Nr. 158093z, Columbus, Ohio, US; M. Laskowski, Jr. et al., "Correlation of Amino Acid Sequence with Inhibitor Activity and Specificity of Protein Inhibitors of Serine Proteinases", COLLOQ. Ges. Biol. Chem. 1981, 32 (Str. Fun.Aspect.Enz Cat. 136-52.

Chemical Abstracts, Band 100, 1984, Seite 241, Zusammenfassung Nr. 116990k, Columbus, Ohio, US; M. Laskowski, Jr. et al.: "Relationshipo between the Amino Acid Sequence and Inhibitory Activity of Protein Inhibitors of Proteinases:, & Proteinase Inhib." 1983, 55-68.

Biological Abstracts, RRM 34:19104, AN 88:42084, Philadelphia, Pa., US; M. Szardenings et al; "Possible Perturbations in Site Directed Mutagenesis due to Secondary Structures in the Single Stranded", & Biol. Chem. Hoppe-Seyler 368 (9), 1987.

```
       Asp Ser Leu Gly Arg Glu Ala Lys Cys Tyr Asn Glu Leu Asn Gly
                2               4                   6
  1    GACTCTCTGGGTCGTGAAGCTAAATGCTACAACGAACTGAACGGT
 45    CTGAGAGACCCAGCACTTCGATTTACGATGTTGCTTGACTTGCCA
           1         3              5

Cys Thr Lys Ile Tyr Asn Pro Val Cys Gly Thr Asp Gly Asp Thr
                8               10              12
 46    TGCACTAAGATCTACAACCCGGTTTGCGGTACCGACGGTGACACT
 90    ACGTGATTCTAGATGTTGGGCCAAACGCCATGGCTGCCACTGTGA
           7       9          11              13

Tyr Pro Asn Glu Cys Val Leu Cys Phe Glu Asn Arg Lys Arg Gln
               14              16                  18
 91    TACCCGAACGAATGCGTTCTGTGCTTCGAAAACCGTAAACGTCAG
135    ATGGGCTTGCTTACGCAAGACACGAAGCTTTTGGCATTTGCAGTC
                       15              17

Thr Ser Ile Leu Ile Gln Lys Ser Gly Pro Cys •••
               20              22              24
136    ACTTCTATCCTGATCCAGAAATCTGGTCCGTGCTGAATTCAAGCT
180    TGAAGATAGGACTAGGTCTTTAGACCAGGCACGACTTAAGTTCGA
               19              21              23

181    TC
186    AGGTAC
       25
```

FIG. 1

α-amylase signal sequence from pALK 1

Eco RI

```
          -100      -90       -80       -70       -60       -50
            *        *         *         *         *         *
GAATTCTCCAGTCTTCACAACAATTGAAAGGAGGAAGCTGAAGAAAGAGTAAGAGGAATT
```

```
           -40       -30       -20       -10        1        10
            *         *         *         *         *         *
TTTGACTCCGCAGTCAGTCTTCAAAAATCAAATAAGGAGTGTCAAAA ATG TTT AAA AAA
                                      SD          Met Phe Lys Lys
```

```
          20              30              40              50              60
           *               *               *               *               *
CGA TTC AAA ACC TCT TTA CTG CCG TTA TTC GCC GGA TTT TTA CTG CTG
Arg Phe Lys Thr Ser Leu Leu Pro Leu Phe Ala Gly Phe Leu Leu Leu
```

```
              70              80              90             100
               *               *               *               *
TTT CAT TTG GTT TTG TCA GGC CCG GCG GCT GCA AAC GCT GAA ACT GCA
Phe His Leu Val Leu Ser Gly Pro Ala Ala Ala Asn Ala Glu Thr Ala
                                          31
```

```
 110          120         130
  *            *  BstEII   *
CAC AAA TCG AAT GAG↓GTG ACC GAT
His Lys Ser Asn Glu Val Thr Asp
                41↑
                   bacillus
                   processing
                   site
```

FIG. 2

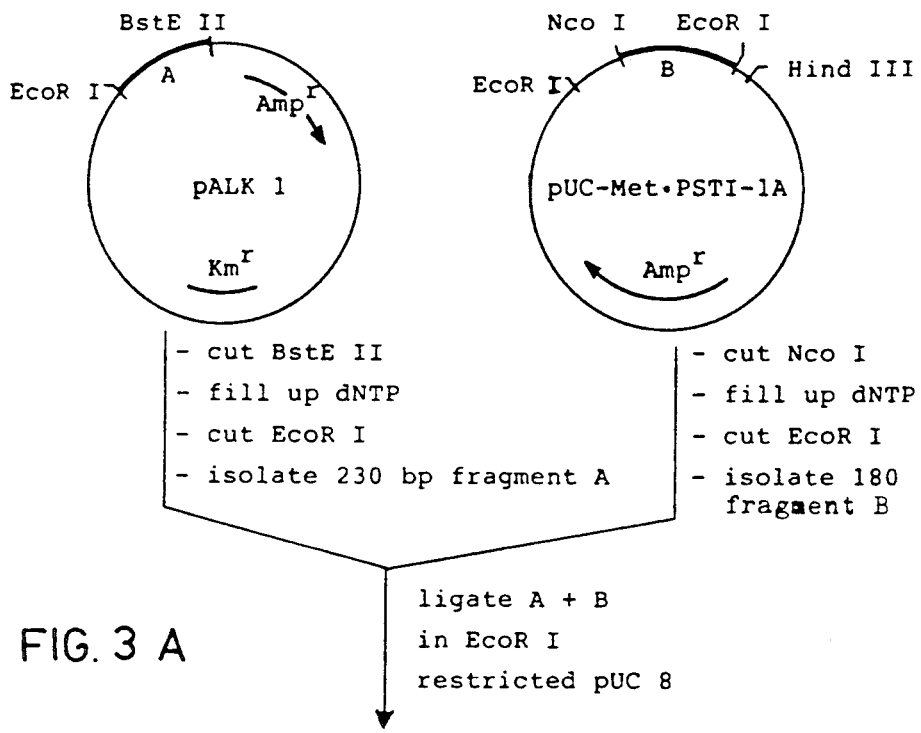
FIG. 3 A
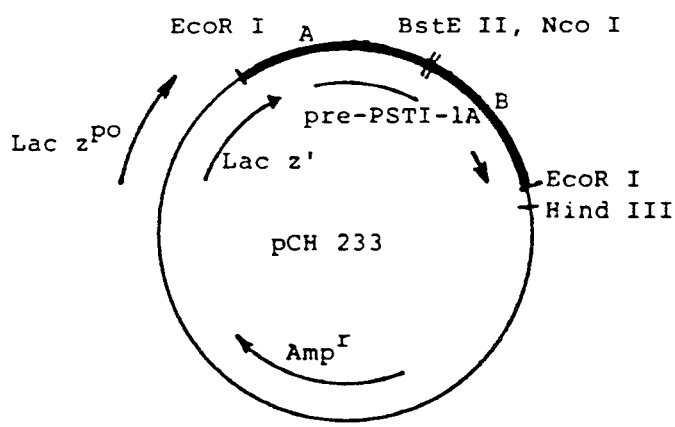
FIG. 3 B
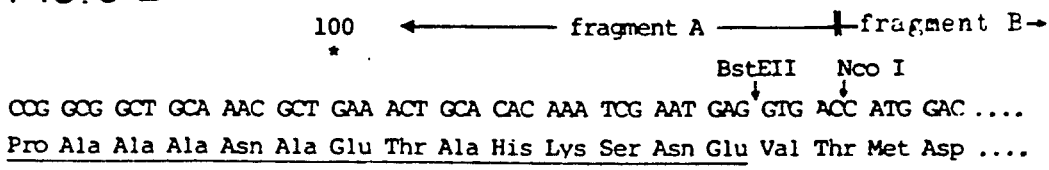

PENAC Sequence

```
                              1                 5                    10
                             Met Lys Asn Arg Asn Arg Met Ile Met Asn Cys
        ◄─────────────────────────── Pass 1 ───────────────────────► ◄────
 1         10         20          30            40                   50
AATTCCTAGAGGATATCATT ATG AAA AAT AGA AAT CGT ATG ATC ATG AAC TGT
    GGATCTCCTATAGTAA TAC TTT TTA TCT TTA GCA TAC TAG TAC TTG ACA
 ↑           ↑                                           ↑
 │       ◄───┤ ◄─────────────── Pass 2 ──────────────┤
 │           │                                           │
EcoRI       EcoRV                                       Bcl I
``` processing site of the PENAC signal sequence

```
            15                  20                   26  ↓
       Val Thr Ala Ser Leu Met Tyr Tyr Trp Ser Leu Pro Ala Leu Ala
       ────────────────────── Pass 3 ──────────────────────────►
              60          70          80          90
       GTT ACT GCT TCC CTG ATG TAT TAT TGG AGC TTA CCT GCA CTG G
       CAA TGA CGA AGG GAC TAC ATA ATA ACC TCG AAT GGA CGT GAC CGATC
       ────────►◄──────────── Pass 4 ──────────────────────┤   ►
                                                            ↑
                                                           Nhe I
```

FIG. 4

PANCREATIC SECRETORY TRYSPIN INHIBITOR AND VARIANTS THEREOF PRODUCED BY A RECOMBINANT HOST THEREFORE AND PHARMACEUTICAL USE THEREOF

This application is a continuation, of application Ser. No. 134,724, filed Dec. 18, 1987, now abandoned.

BACKGROUND OF THE INVENTION

1. Field of the Invention

The present invention relates to a microbially produced peptide having essentially the amino acid sequence of human pancreactic secretory trypsin inhibitor (h-PSTI). The present invention further relates to variants of such peptide wherein one or more of the amino acids in the original sequence are replaced by other amino acids. These peptides show an advantageously modified specificity in their inhibitory action. A method of preparation of the peptides and their pharmaceutical use is also described.

2. Background Information

The lysosomal elastase (leukocyte elastase): J. G. Bieth (1986) p. 217-320 (in Regulation of Matrix Accumulation, Mecham ed., Academic Press, Orlando) from polymorphonuclear granulocytes is a potent intracellular protease which is stored in lysosomes and fulfills its physiological function, the intracellular protein breakdown, in phagolysosomes. The major functional role of lysosomal proteases (elastase, cathepsin G, etc.; H. Fritz et al (1984) in Selected Topics in Clinical Enzymology, Goldberg and Werner ed., Walter de Gruyter, Berlin vol. 2, p. 305-328) is the degradation of phagocytized material from either the organism itself (e.g., metabolic products, injured tissue) or from invasive organisms (bacteria, viruses, molds, etc.).

Upon release into the extracellular space (blood or interstitial fluid) elastase is rapidly bound by potent endogenous inhibitors such as $\alpha_1$-PI ($\alpha_1$-protease inhibitor; J. Travis and G. S. Salvesen, (1983), Ann. Rev. Biochem. p. 655-709,) in plasma, and/or antileukoprotease (also called HUSI-I, human seminal proteinase inhibitor); H. Schiessler et al, (1978), p. 195-207, in Neutral Proteases of Human Polymorphonuclear Leukocytes, Havemann and Janoff ed., Urban & Schwarzenberg, Baltimore) in mucous secretions.

Due to a hereditary $\alpha_1$-PI-deficiency (J. B. Bieth, 1986) or as a consequence of massive extracellular release of elastase (in acute and chronic inflammations, polytrauma or shock; H. Fritz et al, 1984) the protection of the organism against the degradative potential of elastase by natural protease inhibitors is insufficient. An excessive and locally even total consumption of the endogenous protease inhibitors is caused by (i) complex formation with elastase, (ii) proteolytic inactivation by various lysosomal proteases, and (iii) particularly by oxidative inactivation ($\alpha_1$-PI) (J. B. Bieth (1986); H. Fritz et al. (1984); J. Travis and G. S. Salvesen (1983); see above).

The consequence is an extensive proteolytic degradation of connective tissues, as well as of humoral proteins including coagulation-, fibrinolysis-, and complement factors by elastase and other lysosomal proteases (e.g., cathepsin G) leading to severe clinical symptoms like emphysema, shock lung, adult respiratory distress syndrome, coagulation disorders, kidney and liver failure, etc. (additionally to the above references: Neue Wege in der Entzündungsdiagnostik, PMN Elastase; M. Jochum et al (ed), (1985), GIT Verlag, Darmstadt: C. T. Lee et al, (1981) N. Engl. J. Med., 304, 192-196; W. W. McGuire et al, (1982), J. Clin. Invest., 69, 543).

Elastase contributes also to the local inflammatory event going on in rheumatoid arthritis, e.g., the degradation of connective tissue constituents (K. Kleesiek et al (1985) in Neue Wege in der Entzündungsdiagnostik, PMN Elastase, p. 71-82).

The extracellular release of elastase after severe injuries or in diseases like septic shock, shock lung, etc. can be monitored routinely by means of enzyme immunoassays (S. Neumann and M. Jochum, (1984), p. 184-195 in Methods of Enzymatic Analysis, Bergmeyer (ed), Verlag Chemie, Weinheim).

In experimental models of sepsis and emphysema, synthetic elastase inhibitors (J. C. Powers, Am. Rev. Respir. Dis., (1983), 127, 554-558) and natural inhibitors from animals such as eglin C (H. P. Schnebli et al, (1985), Eur. J. Respir. Dis., 66, Suppl. 139 p. 66-70) have proven to be therapeutically useful. The application of a protease inhibitor of human origin would be preferable in order to avoid toxic side effects and especially allergic reactions when a prolonged therapy is indicated, e.g., in the treatment of $\alpha_1$-PI deficiency (emphysema). Since the human $\alpha_1$-PI is a glycoprotein of high molecular weight, its production in sufficient amounts by means of gene technology is not feasible in the near future.

The antileucoprotease or HUSI-I (H. Schiessler et al, 1978; and U. Seemüller et al, (1986), FEBS Letters 199, 43-48) has a MW of 14,000 Dalton and consists of two active domains, one directed against elastase, the other against trypsin. Hence this type of inhibitor has a relative low selectivity and is not a specific elastase inhibitor. Inhibition of trypsin or trypsin-like enzymes is normally not intended in the indications given above.

The human pancreas secretes the PSTI, a protease inhibitor of low MW (6.2 kd) which specifically inhibits trypsin, i.e., it possesses a high selectivity for one specific type of protease.

One advantage presented in this invention consists in substitution by recombinant DNA technology of only one (or a few) amino acids in the PSTI yielding PSTI variants which were shown to be highly effective protease inhibitors with high specificity for leukocyte elastase. Moreover, due to its relatively low MW the elastase PSTI derivative complex should pass through the kidney as well. Therefore, elimination of extracellularly released elastase will be highly efficient. The fact that PSTI is of human origin, taken together with its low MW lead applicants to expect that the clinical application of PSTI derivatives will be devoid of complications due to recognition of these substances as foreign proteins by the immune system.

Another essential advantage of PSTI compared to $\alpha_1$-PI and antileukoprotease is the insensitivity to oxidative inactivation during inflammatory processes whereby strongly oxidative agents are produced and released extracellularly. Consequently, compared to $\alpha_1$-PI or antileukoprotease, lower doses of the PSTI derivative should be sufficient to achieve a similar protective effect.

SUMMARY OF THE INVENTION

It is therefore an object of the present invention to provide pharmaceutically useful peptides having proteinase inhibitor activity preferably with an improved specificity and/or improved inhibitory efficiency. Said peptides are peptides having the sequence of pancreatic secretory trypsin inhibitor (PSTI) and variants thereof which are produced by recombinant DNA technology. The term "variants" refers to peptides wherein one or more of the amino acids in the parent sequence are replaced by another of the naturally occurring amino acids. As a parent sequence, the sequence of human pancreatic trypsin inhibitor (h-PSTI = PSTI 0) is used. Preferred positions to be subjected to the replacement of amino acids are the positions 17, 18, 19, 20, 21, 29, 32 and 36 in the peptide. More specifically the present invention relates to peptides having essentially the sequence of PSTI 0 (as reported by L. J. Greene, 1976. Methods Enzymol., 45, 813-825) comprising the amino acids Glu. Asp or Leu in position 13;
Glu. Asp or Asn in position 14;
Thr. Pro, Ser, Arg, Leu or Met in position 17;
Leu. Met, Val, Gln. Ser, Ala, Thr, Ile, Tyr, Phe, Arg, Trp or Lys in position 18;
Glu. Asp, Leu or Ile in position 19;
Tyr. Phe, Asp, Asn, Leu, Glu, Gln, His or Arg in position 20;
Glu. Arg, Met, Phe, Lys, Val, Thr, Gln, Leu, Asp or Asn in position 21;
Lys, Glu, Ile, Gln, Asp or Asn in position 29;
Pro, Gly, Ser, Asn, Ala, Asp, Val, Arg or His in position 32; and
Asn. Asp, Ala, Ser, Gly, Tyr, Val or Glu in position 36 with the exception of the combinations Leu13-Asn14-Thr17-Lys18-Ile19-Tyr20-Asn21-Asp29-Pro32-Val36 and Leu13-Asn14-Thr17-Lys18-Ile19-Tyr20-Asp21-Asn29-Pro32-Val36.

Table 1 hereinbelow refers to some of the variants. PSTI 0 is the parent sequence if the amino acids in positions 32 and 36 are proline and valine respectively.

tain in position −1 a methionine or a leader peptide. Term "leader peptide" in connection with the present invention refers not only to signal sequences promoting secretion of the expression product (S. D. Emr et al., J. of Cell Biol., 1980, 86, p. 701-711) but also to peptides containing a signal sequence and a linker sequence preceeding the PSTI sequences.

TABLE 1

| Position | PSTI - variants | | | | | |
|---|---|---|---|---|---|---|
| | 17 | 18 | 19 | 20 | 21 | 29 |
| PSTI 0 | Thr | Lys | Ile | Tyr | Asn | Asp |
| PSTI 1 | Thr | Leu | Ile | Tyr | Asn | Asp |
| PSTI 2 | Thr | Leu | Ile | Tyr | Asp | Asn |
| PSTI 3 | Thr | Tyr | Glu | Tyr | Arg | Asp |
| PSTI 4 | Thr | Leu | Glu | Tyr | Arg | Asp |
| PSTI 5 | Thr | Val | Glu | Tyr | Arg | Asp |
| PSTI 6 | Thr | Leu | Glu | Tyr | Asn | Asp |
| PSTI 7 | Thr | Leu | Ile | Tyr | Arg | Asp |
| PSTI 8 | Thr | Val | Glu | Leu | Asn | Asp |
| PSTI 9 | Thr | Val | Glu | Leu | Arg | Asp |
| PSTI 10 | Pro | Lys | Ile | Tyr | Asp | Asn |
| PSTI 11 | Pro | Leu | Glu | Tyr | Arg | Asp |
| PSTI 12 | Pro | Val | Glu | Tyr | Arg | Asp |
| PSTI 13 | Thr | Ile | Glu | Tyr | Asn | Asp |
| PSTI 14 | Thr | Arg | Glu | Tyr | Asn | Asp |
| PSTI 15 | Thr | Phe | Glu | Tyr | Asn | Asp |
| PSTI 16 | Thr | Ala | Glu | Tyr | Asn | Asp |
| PSTI 17 | Thr | Val | Ile | Tyr | Asn | Asp |
| PSTI 18 | Thr | Ile | Ile | Tyr | Asn | Asp |
| PSTI 19 | Thr | Val | Ile | Tyr | Asp | Asn |
| PSTI 20 | Thr | Ile | Ile | Tyr | Asp | Asn |
| PSTI 21 | Thr | Ile | Glu | Tyr | Arg | Asp |
| PSTI 22 | Thr | Tyr | Ile | Tyr | Asn | Asp |
| PSTI 23 | Thr | Phe | Ile | Tyr | Asn | Asp |
| PSTI 24 | Thr | Lys | Glu | Tyr | Arg | Asp |

The present invention also relates to the DNA's coding for said peptides. In particular the present invention is related to a DNA, hereinbelow called "master gene", having the sequence

```
    Asp Ser Leu Gly Arg   Glu Ala Lys Cys Tyr   Asn Glu Leu Asn Gly
          2                   4                     6
 1  /GACTCTCTGGGTC\/GTGAAGCTAAATGCTAC\/AACGAACTGAACGGT

45  \CTGAGAG/\ACCCAGCACTTCGATT/\TACGATGTTGCTTGAC/\TTGCCA
          1              3                 5

Cys  Thr Lys Ile Tyr   Asn Pro Val Cys   Gly Thr Asp Gly Asp Thr
             8                    10                  12
46  TG\/CACTAAGATCTAC\/AACCCGGTTTGCGG\/TACCGACGGTGACAC\/T

90  ACGTGATTC/\TAGATGTTGGGC/\CAAACGCCATGGCTG/\CCACTGTGA
         7              9                11                13

Tyr Pro Asn Glu Cys   Val Leu Cys Phe Glu Asn   Arg Lys Arg Gln
              14                   16                      18
91  TACCCGAACGAATGC\/GTTCTGTGCTTCGAAA\/ACCGTAAACGTCAG

135 ATGGGCT/\TGCTTACGCAAGACAC/\GAAGCTTTTGGCATTT/\GCAGTC
          15                      17

Thr Ser Ile Leu Ile Gln   Lys Ser Gly Pro Cys   . . .
                 20                   22                   24
136 AC\/TTCTATCCTGATCCA\/GAAATCTGGTCCGTG\/CTGAATTCAAGCT

180 TGAAGATAGG/\ACTAGGTCTTTAGAC/\CAGGCACGACTTAA/\GTTCGA
           19                   21                    23

181 TC\

186 AGGTAC/
        25
```

The variants disclosed in Table 1 can be further varied in position 32 and 36 by the aminoacids listed above.

The present invention also relates to peptides having the sequences as outlined above which in addition conand functional equivalents thereof. The meaning of "functional equivalents" is that also derivatives of the above DNA sequence may be useful for the expression of the same protein. It is known to those skilled in the art that in some codons one, or two, or three of the bases can be replaced by another base without having an effect on the amino acid to be incorporated in a given protein. In order to produce variants of the peptide the master gene is modified by means of DNA-technology in such manner that the codon for an amino acid in a particular position is replaced by a codon for another aminoacid. To obtain a DNA coding for one of the variant peptides according to the present invention the codons for the aminoacids in positions 17, 18, 19, 20, 21, 29, 32 and 36 can be replaced by other codons.

Preferred codons in such replacements are the codons coding for the amino acids as listed above. Depending on the expression system used the DNA of the present invention can also be a DNA coding for one of the above peptides additionally carrying upstream a sequence coding for a leader peptide.

A further object of the present invention is an expression vector also called a plasmid comprising the DNA coding for one of the peptides of the present invention. The plasmid is used for the transformation of a host-organism. The present invention also relates to such transformed microorganisms. A large number of various microorganisms are known to those skilled in the art as being suitable for transformation. The nature of the plasmid is mainly dependent on the host organism to be used.

The host organism transformed with the plasmid comprising the DNA of the present invention is used in the production of the above peptide and variants thereof. The production comprises the steps of
a) cultivating the host organism under appropriate conditions,
b) recovering the peptide from the culture and
c) purifying the peptide.

The purification of the peptide may be achieved by known methods of protein chemistry, as for example, precipitation, chromatography and electrophoresis. The above mentioned linker peptide can be a good tool in such purification since it can be used advantageously as a purification handle. If, for example, the linker peptide comprises mainly basic or acid amino acids, ion-exchange chromatography may be very useful in the purification of the expressed product.

The present invention also relates to pharmaceutical compositions and preparations comprising the peptides as outlined above and the use of said peptides in the preparation of pharmaceutical compositions. Such pharmaceutical compositions are very useful in the indications described above.

The pharmaceutical preparations in addition to non-toxic, inert pharmaceutically suitable excipients can contain one or more compounds according to the invention or consist of one or more active compounds according to the invention.

BRIEF DESCRIPTION OF THE DRAWINGS

FIG. 1 is a nucleotide and corresponding amino acid sequence of the PSTI master gene.

FIG. 2 is a DNA sequence of the 230 bp EcoRI-BstEII fragment from pALK1.

FIGS. 3A and 3B depict a schematic diagram for the construction of pCH 233.

FIG. 3B depicts the sequences at the junction between the α-amylase signal sequence (fragment A) and the Met-PSTI gene (fragment B) for either Met-PSTI-1A or -4A.

FIG. 4 depicts a synthetic EcoRI-NheI DNA fragment (PENAC) and a modified signal sequence of E. coli penicillin acylase.

DETAILED DESCRIPTION OF THE INVENTION

Figure 5A:
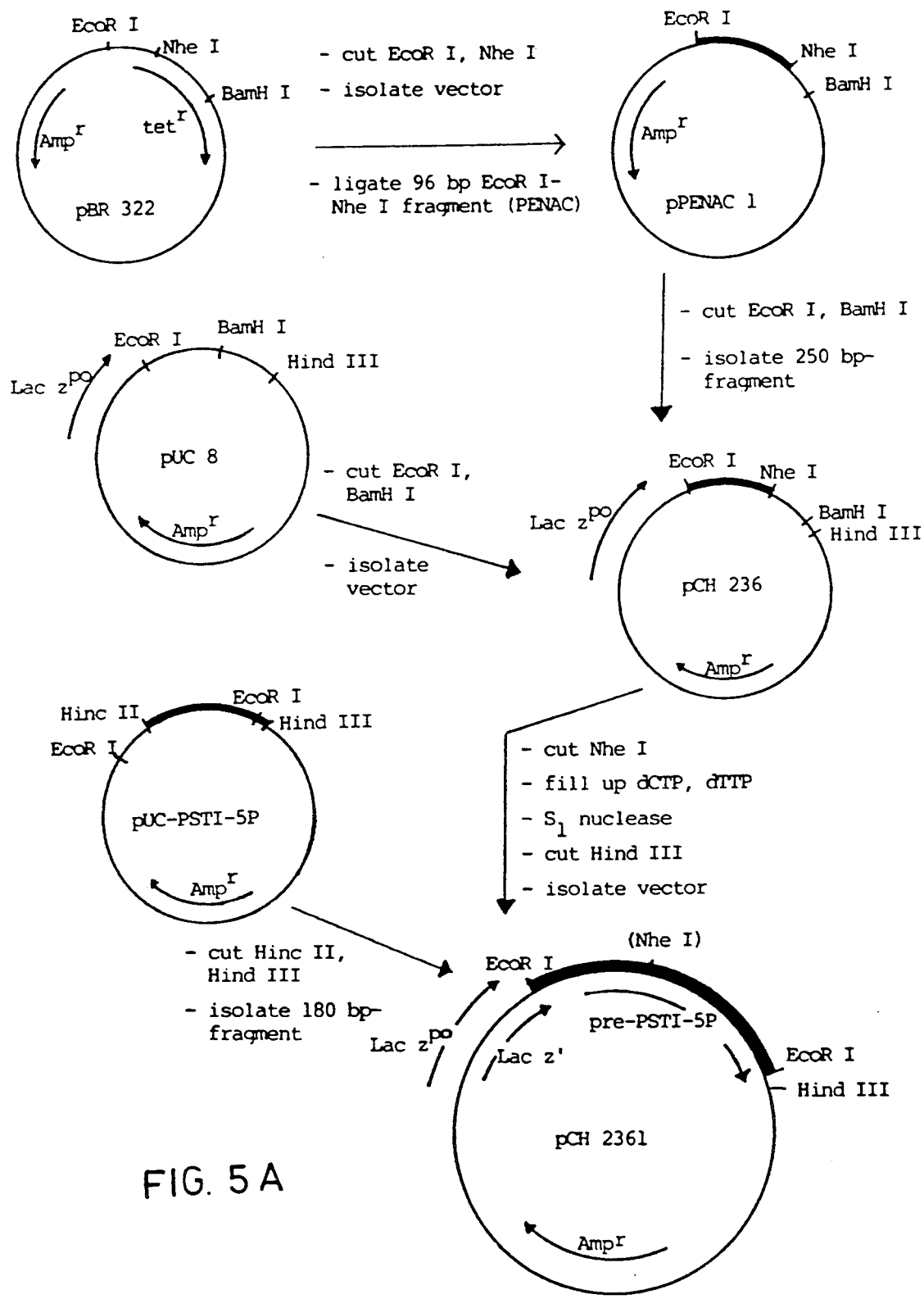
FIG. 5A depicts a schematic diagram for the construction of pCH 236 and pCH 2361 (pCH 2362).

The present invention also includes pharmaceutical preparations in dosage units. This means that the preparations are in the form of individual parts, for example, tablets, coated tablets, capsules, pills, suppositories and ampoules, of which the content of active compound corresponds to a fraction or a multiple of an individual dose. The dosage units can contain, for example, one, two, three or four individual doses or one half, one third or one quarter or an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example, starches, lactose, sucrose, glucose, mannitol and silica, (b) binders, for example, carboxymethylcellulose, alginates, gelatin and polyvinylpyrrolidone, (c) humectants, for example, glycerol, (d) disintegrants, for example, agar-agar, calcium carbonate and sodium carbonate, (e) solution retarders, paraffin and (f) absorption accelerators, for example, quaternary ammonium compounds, (g) wetting agents, for example, cetyl alcohol and glycerol monostearate, (h) adsorbents, for example, kaolin and bentonite and (i) lubricants, for example, talc, calcium and magnesium stearate and solid polyethylene glycols, or mixtures of the substances listed under (a) to (i) above.

The tablets, coated tablets, capsules, pills and granules can be provided with the customary coatings and shells, optionally containing opacifying agents, and can also be of such composition that they release the active compound or compounds only, for preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example, polyethylene glycols, fats, for example, cacao fat and higher esters (for example $C_{14}$ alcohol with $C_{16}$ fatty acid) or mixtures of these substances.

Ointments, pastes, creams and gels can contain the customary excipients in addition to the active compound or compounds, for example, animal and vegetable fats, waxes, paraffins, starch, tragacanth, cellulose derivatives, polyethylene glycols, silicones, bentonites, silica, talc and zinc oxide, or mixtures of these substances.

Powders and sprays can contain the customary excipients in addition to the active compound or compounds, for example, lactose, talc, silica, aluminium hydroxide, calcium silicate and polyamide powders, or mixtures of these substances. Sprays can additionally contain the customary propellants, for example, chlorofluorohydrocarbons.

Solutions and emulsions can contain the customary excipients in addition to the active compound or compounds, such as solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solution and emulsions can also be in a sterile form which is isotonic with blood.

Suspensions can contain the customary excipients in addition to the active compound or compounds, such as liquid diluents, for example, water, ethyl alcohol or propylene glycol, suspending agents, for example, ethoxylated isostearyl alcohols, polyoxyethylene sorbitol and sorbitan esters, microcrystalline cellulose, aluminium metahydroxide, bentonite, agar-agar and tragacanth, or mixtures of these substances.

The formulation forms mentioned can also contain dyestuffs, preservatives and additives which improve the odor and flavor, for example, peppermint oil and eucalyptus oil, and sweeteners, for example, saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example, by mixing the active compound or compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100, mg/kg of body weight every 24 hours, optionally in the form of several individual administration, in order to achieve the desired results. An individual administration contains the active compound or compounds according to the invention preferably in amounts of about 1 to about 250, in particular 3 to 60, mg/kg of body weight. However, it can be necessary to deviate from the dosages mentioned and, in particular, to do so as a function of the nature and body weight of the subject to be treated, the nature and severity of the illness, the nature of the preparation and of the administration of the medicine, and the time or interval over which the administration takes place.

Thus, it can suffice in some cases to manage with less than the abovementioned amount of active compound, whilst in other cases the abovementioned amount of active compound must be exceeded. The particular required optimum dosage and the type of administration of the active compounds can easily be decided by anyone skilled in the art on the basis of his expert knowledge.

PSTI may be isolated from the pancreas, but is not available in large quantities especially such PSTI of human origin.

It was therefore perceived that the application of recombinant DNA and associated technologies would be the effective way of providing the necessary large quantities of high quality h-PSTI and also of variants of such peptide. The production of a foreign protein in recombinant bacteria is not trivial in the light of the known instabilities found in many cases (B. E. Butterworth and B. D. Kovant: J. Virol., 14, (1984), 282–291, D. V. Goeddel et al: Proc. Natn. Acad. Sci. USA, 76, (1979), 106–110, M. Inouye et al in "The future in nucleic acid research", I. Watanable ed., (Tokyo, Academic Press), (1983)). The instability is in particular a problem in the expression of peptides having a relatively short chain length.

The human pancreas secretes the PSTI, a protease inhibitor of low MW (6.2 kd) which specifically inhibits trypsin, i.e. it possesses a high selectivity for one specific type of protease.

One advantage presented in this invention consists in substitution by recombinant DNA technology of only one (or a few) amino acids in the PSTI yielding PSTI variants which were shown to be highly effective protease inhibitors with high specificity for leukocyte elastase. Moreover, due to its relatively low MW the elastase PSTI derivative complex should pass through the kidney as well. Therefore, elimination of extracellularly released elastase will be highly efficient. The fact that PSTI is of human origin taken together with its low MW lead applicants to expect that the clinical application of PSTI derivatives will be devoid of complications due to recognition of these substances as foreign proteins by the immune system.

Another essential advantage of PSTI compared to $\alpha_1$-PI and Antileukoprotease is the insensitivity to oxidative inactivation during inflammatory processes whereby strongly oxidative agents are produced and released extracellularly. Consequently, compared to $\alpha_1$-PI or antileukoprotease lower doses of the PSTI derivative should be sufficient to achieve a similar protective effect.

THE GENE SEQUENCES

The amino acid sequence of h-PSTI was back-translated into a DNA master gene sequence with the use of those codons which are most frequently found in highly expressed *E. coli* genes (Gouy. M. and Gautier. C., (1982), Nucleic Acids Res., 10, 7055-7074), see FIG. 1. For amino acid substitutions of the PSTI variants (Table 1) the corresponding codons were exchanged in the master gene (see Table 2 hereinbelow).

Codons marked with an asterix in Table 2 were used throughout, with the following exceptions:

Thr 26 (ACC)—In all genes, to create a KpnI-site at positions 72-77

Lys 18 (AAG)—in PSTI-0, and -10, to create a BglII-site at positions 53-58

Gly 28 (GGC)—In PSTI-2, -10, -19 and -20 to achieve proper hybridization of the corresponding oligonucleotide fragments (see below)

Pro 17 (CCT)—in PSTI 11, to create a XbaI-site at +Leu 18 (CTA) positions 51-56

5'-terminus of the gene: first codon, comprises the second half of the HincII-site GTPyPuAC.

3'-terminus of the gene: stop-codon TGA overlapping the EcoRI-site (position 170-175) followed by a HindIII-site (position 176-181) and a NcoI sticky end (position 182-186)

TABLE 2

| Codon usage table |  |  |  |  |  |  |  |  |
|---|---|---|---|---|---|---|---|---|
| Ala | Arg | Asp | Asn | Cys | Glu | Gln | Gly | His | Ile |
| GCA | AGA | GAC* | AAC* | UGC* | GAA* | CAA | GGA | CAC | AUA |
| GCC | AGG | GAU | AAU | UGU | GAG | CAG* | GGC | CAU | AUC* |
| GCG | CGA |  |  |  |  |  | GGG |  | AUU |
| GCU* | CGC |  |  |  |  |  | GGU* |  |  |
|  | CGG |  |  |  |  |  |  |  |  |
|  | CGU* |  |  |  |  |  |  |  |  |

| Leu | Lys | Met | Phe | Pro | Ser | Thr | Trp | Tyr | Val | STOP |
|---|---|---|---|---|---|---|---|---|---|---|
| UUA | AAA* | AUG | UUC* | CCA | AGC | ACA | UGG | UAC* | GUA | UAA |
| UUG | AAG |  | UUU | CCC | AGU | ACC |  | UAU | GUC | UAG |
| CUA |  |  |  | CCG* | UCA | ACG |  |  | GUG | UGA* |
| CUC |  |  |  | CCU | UCC | ACU* |  |  | GUU* |  |
| CUG* |  |  |  |  | UCG |  |  |  |  |  |
| CUU |  |  |  |  | UCU* |  |  |  |  |  |

Briefly the PSTI-gene construction is as follows:

1. Synthesis of 25 short oligonucleotides (12 and 13 respectively, for each complementary strand)

```
   2          22    24
——————— ...... ——— ———
——— ———   ....  ——— ———
 1   3          23   25
``` whereby for some variants specific fragments were synthesised (see Table 3 hereinbelow). Purification of the correct sized fragment by ion exchange High Performance Liquid Chromatography (HPLC).

2. Ligation of the fragments to give a double strand molecule for the coding region for mature PSTI (amino acids 1-56) with a "blunt" end at the amino-terminal coding end and a GATC-single stranded 5'-extended tail at the carboxy-terminal coding end. For this step it was important to optimize the oligonucleotide sequences to be synthesised in order to minimize false ligation products.

3. Cloning in various vectors e.g. pUC8, pGV451, M13mp18 for sequencing (see Methods text).

4. Creation of further variants via single strand mutagenesis in M13-phage vectors using specific synthetic oligonucleotides.

TABLE 3

| | Meaning of the numbers: |
|---|---|
| Column 1: | the fragment numbers (see FIG. 1) |
| Columns 2 and 3: | first and last nucleotide positions of the fragment within the master gene sequence (5' → 3') |
| Column 4: | nucleotide sequence of the fragments (5' → 3') | dots indicate fragments which differ from the master gene sequence and which are required for the construction of the gene variants.

PSTI 0 (Segment I) - master gene
List fragments 1 to 11:

| | | |
|---|---|---|
| 1 | 7 | 1 GAGAGTC |
| 2 | 1 | 13 GACTCTCTGGGTC |
| 3 | 23 | 8 TTAGCTTCACGACCCA |
| 4 | 14 | 30 GTGAAGCTAAATGCTAC |
| 5 | 39 | 24 CAGTTCGTTGTAGCAT |
| 6 | 31 | 47 AACGAACTGAACGGTTG |
| 7 | 54 | 40 CTTAGTGCAACCGTT |
| 8 | 48 | 60 CACTAAGATCTAC |
| 9 | 66 | 55 CGGGTTGTAGAT |
| 10 | 61 | 74 AACCCGGTTTGCGG |
| 11 | 81 | 67 GTCGGTACCGCAAAC |

PSTI-0 (Segment II) - master gene
List fragments 12 to 25:

| | | |
|---|---|---|
| 12 | 75 | 89 TACCGACGGTGACAC |
| 13 | 97 | 82 TCGGGTAAGTGTCACC |
| 14 | 90 | 105 TTACCCGAACGAATGC |
| 15 | 113 | 98 CACAGAACGCATTCGT |
| 16 | 106 | 121 GTTCTGTGCTTCGAAA |
| 17 | 129 | 114 TTTACGGTTTTCGAAG |
| 18 | 122 | 137 ACCGTAAACGTCAGAC |
| 19 | 145 | 130 GGATAGAAGTCTGACG |
| 20 | 138 | 152 TTCTATCCTGATCCA |
| 21 | 160 | 146 CAGATTTCTGGATCA |
| 22 | 153 | 167 GAAATCTGGTCCGTG |
| 23 | 174 | 161 AATTCAGCACGGAC |
| 24 | 168 | 182 CTGAATTCAAGCTTC |
| 25 | 186 | 175 CATGGAAGCTTG |

PSTI 1 (Segment I)
List fragments 1 to 11:

| | | |
|---|---|---|
| 1 | 7 | 1 GAGAGTC |
| 2 | 1 | 13 GACTCTCTGGGTC |
| 3 | 23 | 8 TTAGCTTCACGACCCA |
| 4 | 14 | 30 GTGAAGCTAAATGCTAC |
| 5 | 39 | 24 CAGTTCGTTGTAGCAT |
| 6 | 31 | 47 AACGAACTGAACGGTTG |
| •7 | 54 | 40 CAGAGTGCAACCGTT |
| •8 | 48 | 60 CACTCTGATCTAC |
| 9 | 66 | 55 CGGGTTGTAGAT |
| 10 | 61 | 74 AACCCGGTTTGCGG |
| 11 | 81 | 67 GTCGGTACCGCAAAC |

PSTI 2 (Segment I)

TABLE 3-continued

List fragments 1 to 11

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | CAGAGTGCAACCGTT |
| •8 | 48 | 60 | CACTCTGATCTAC |
| •9 | 66 | 55 | CGGGTCGTAGAT |
| •10 | 61 | 74 | GACCCGGTTTGCGG |
| 11 | 81 | 67 | GTCGGTACCGCAAAC |

PSTI 3 (Segment I)
List fragments 1 to 11.

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | GTAAGTGCAACCGTT |
| •8 | 48 | 60 | CACTTACGAATAC |
| •9 | 66 | 55 | CGGACGGTATTC |
| •10 | 61 | 74 | CGTCCGGTTTGCGG |
| 11 | 81 | 67 | GTCGGTACCGCAAAC |

PSTI 4 (Segment I)
List fragments 1 to 11.

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | CAGAGTGCAACCGTT |
| •8 | 48 | 60 | CACTCTGGAATAC |
| •9 | 66 | 55 | CGGACGGTATTC |
| •10 | 61 | 74 | CGTCCGGTTTGCGG |
| 11 | 81 | 67 | GTCGGTACCGCAAAC |

PSTI 5 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | AACAGTGCAACCGTT |
| •8 | 48 | 60 | CACTGTTGAATAC |
| •9 | 66 | 55 | CGGACGGTATTC |
| •10 | 61 | 74 | CGTCCGGTTTGCGG |
| 11 | 81 | 67 | GTCGGTACCGCAAAC |

PSTI 6 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | CAGAGTGCAACCGTT |
| •8 | 48 | 60 | CACTCTGGAATAC |
| •9 | 66 | 55 | CGGGTTGTATTC |
| 10 | 61 | 74 | AACCCGGTTTGCGG |
| 11 | 81 | 67 | GTCGGTACCGCAAAC |

PSTI 7 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | CAGAGTGCAACCGTT |
| •8 | 48 | 60 | CACTCTGATCTAC |
| •9 | 66 | 55 | CGGACGGTAGAT |
| •10 | 61 | 74 | CGTCCGGTTTGCGG |
| 11 | 81 | 67 | GTCGGTACCGCAAAC |

PSTI 13 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | GATAGTGCAACCGTT |
| •8 | 48 | 60 | CACTATCGAATAC |
| •9 | 66 | 55 | CGGGTTGTATTC |
| 10 | 61 | 74 | AACCCGGTTTGCGG |
| 11 | 81 | 67 | GTCGGTACCGCAAAC |

PSTI 14 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | ACGAGTGCAACCGTT |
| •8 | 48 | 60 | CACTCGTGAATAC |
| •9 | 66 | 55 | CGGGTTGTATTC |
| 10 | 61 | 74 | AACCCGGTTTGCGG |
| 11 | 81 | 67 | GTCGGTACCGCAAAC |

PSTI 15 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | GAAAGTGCAACCGTT |
| •8 | 48 | 60 | CACTTTCGAATAC |
| •9 | 66 | 55 | CGGGTTGTATTC |
| 10 | 61 | 74 | AACCCGGTTTGCGG |
| 11 | 81 | 67 | GTCGGTACCGCAAAC |

PSTI 16 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | AGCAGTGCAACCGTT |
| •8 | 48 | 60 | CACTGCTGAATAC |
| •9 | 66 | 55 | CGGGTTGTATTC |
| 10 | 61 | 74 | AACCCGGTTTGCGG |
| 11 | 81 | 67 | GTCGGTACCGCAAAC |

PSTI 17 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | AACAGTGCAACCGTT |
| •8 | 48 | 60 | CACTGTTATCTAC |
| 9 | 66 | 55 | CGGGTTGTAGAT |
| 10 | 61 | 74 | AACCCGGTTTGCGG |
| 11 | 81 | 67 | GTCGGTACCGCAAAC |

PSTI 18 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |
| 5 | 39 | 24 | CAGTTCGTTGTAGCAT |
| 6 | 31 | 47 | AACGAACTGAACGGTTG |
| •7 | 54 | 40 | GATAGTGCAACCGTT |
| •8 | 48 | 60 | CACTATCATCTAC |
| 9 | 66 | 55 | CGGGTTGTAGAT |
| 10 | 61 | 74 | AACCCGGTTTGCGG |
| 11 | 81 | 67 | GTCGGTACCGCAAAC |

PSTI 19 (Segment I)
List fragments 1 to 11:

| | | | |
|---|---|---|---|
| 1 | 7 | 1 | GAGAGTC |
| 2 | 1 | 13 | GACTCTCTGGGTC |
| 3 | 23 | 8 | TTAGCTTCACGACCCA |
| 4 | 14 | 30 | GTGAAGCTAAATGCTAC |

TABLE 3-continued

|   |     |     |                 |
|---|-----|-----|-----------------|
| 5 | 39  | 24  | CAGTTCGTTGTAGCAT |
| 6 | 31  | 47  | AACGAACTGAACGGTTG |
| •7 | 54 | 40  | AACAGTGCAACCGTT |
| •8 | 48 | 60  | CACTGTTATCTAC |
| •9 | 66 | 55  | CGGGTCGTAGAT |
| •10 | 61 | 74 | GACCCGGTTTGCGG |
| 11 | 81 | 67  | GTCGGTACCGCAAAC |

PSTI 20 (Segment I)
List fragments 1 to 11:

|    |    |    |                  |
|----|----|----|------------------|
| 1  | 7  | 1  | GAGAGTC          |
| 2  | 1  | 13 | GACTCTCTGGGTC    |
| 3  | 23 | 8  | TTAGCTTCACGACCCA |
| 4  | 14 | 30 | GTGAAGCTAAATGCTAC |
| 5  | 39 | 24 | CAGTTCGTTGTAGCAT |
| 6  | 31 | 47 | AACGAACTGAACGGTTG |
| •7 | 54 | 40 | GATAGTGCAACCGTT  |
| •8 | 48 | 60 | CACTATCATCTAC    |
| •9 | 66 | 55 | CGGGTCGTAGAT     |
| •10 | 61 | 74 | GACCCGGTTTGCGG  |
| 11 | 81 | 67 | GTCGGTACCGCAAAC  |

PSTI-A (Segment II)
List fragments 12 to 25:

|    |     |     |                  |
|----|-----|-----|------------------|
| 12 | 75  | 89  | TACCGACGGTGACAC  |
| •13 | 97 | 82  | TAGCGTAAGTGTCACC |
| •14 | 90 | 105 | TTACGCTAACGAATGC |
| 15 | 113 | 98  | CACAGAACGCATTCGT |
| 16 | 106 | 121 | GTTCTGTGCTTCGAAA |
| 17 | 129 | 114 | TTTACGGTTTTCGAAG |
| 18 | 122 | 137 | ACCGTAAACGTCAGAC |
| 19 | 145 | 130 | GGATAGAAGTCTGACG |
| 20 | 138 | 152 | TTCTATCCTGATCCA  |
| 21 | 160 | 146 | CAGATTTCTGGATCA  |
| 22 | 153 | 167 | GAAATCTGGTCCGTG  |
| 23 | 174 | 161 | AATTCAGCACGGAC   |
| 24 | 168 | 182 | CTGAATTCAAGCTTC  |
| 25 | 186 | 175 | CATGGAAGCTTG     |

PSTI-S (Segment II)
List fragments 12 to 25:

|    |     |     |                  |
|----|-----|-----|------------------|
| 12 | 75  | 89  | TACCGACGGTGACAC  |
| •13 | 97 | 82  | TAGAGTAAGTGTCACC |
| •14 | 90 | 105 | TTACTCTAACGAATGC |
| 15 | 113 | 98  | CACAGAACGCATTCGT |
| 16 | 106 | 121 | GTTCTGTGCTTCGAAA |
| 17 | 129 | 114 | TTTACGGTTTTCGAAG |
| 18 | 122 | 137 | ACCGTAAACGTCAGAC |
| 19 | 145 | 130 | GGATAGAAGTCTGACG |
| 20 | 138 | 152 | TTCTATCCTGATCCA  |
| 21 | 160 | 146 | CAGATTTCTGGATCA  |
| 22 | 153 | 167 | GAAATCTGGTCCGTG  |
| 23 | 174 | 161 | AATTCAGCACGGAC   |
| 24 | 168 | 182 | CTGAATTCAAGCTTC  |
| 25 | 186 | 175 | CATGGAAGCTTG     |

PSTI 2, 10, 19 and 20 (Segment II)
List fragments 12 to 25:

|    |     |     |                  |
|----|-----|-----|------------------|
| •12 | 75 | 89  | TACCGACGGCAACAC  |
| •13 | 97 | 82  | TCGGGTAAGTGTTGCC |
| 14 | 90  | 105 | TTACCCGAACGAATGC |
| 15 | 113 | 98  | CACAGAACGCATTCGT |
| 16 | 106 | 121 | GTTCTGTGCTTCGAAA |
| 17 | 129 | 114 | TTTACGGTTTTCGAAG |
| 18 | 122 | 137 | ACCGTAAACGTCAGAC |
| 19 | 145 | 130 | GGATAGAAGTCTGACG |
| 20 | 138 | 152 | TTCTATCCTGATCCA  |
| 21 | 160 | 146 | CAGATTTCTGGATCA  |
| 22 | 153 | 167 | GAAATCTGGTCCGTG  |
| 23 | 174 | 161 | AATTCAGCACGGAC   |
| 24 | 168 | 182 | CTGAATTCAAGCTTC  |
| 25 | 186 | 175 | CATGGAAGCTTG     |

PSTI 21 (Segment I)
List fragments 1 to 11:

|    |    |    |                  |
|----|----|----|------------------|
| 1  | 7  | 1  | GAGAGTC          |
| 2  | 1  | 13 | GACTCTCTGGGTC    |
| 3  | 23 | 8  | TTAGCTTCACGACCCA |
| 4  | 14 | 30 | GTGAAGCTAAATGCTAC |
| 5  | 39 | 24 | CAGTTCGTTGTAGCAT |
| 6  | 31 | 47 | AACGAACTGAACGGTTG |
| •7 | 54 | 40 | GATAGTGCAACCGTT  |
| •8 | 48 | 60 | CACTATCGAATAC    |
| •9 | 66 | 55 | CGGACGGTATTC     |
| •10 | 61 | 74 | CGTCCGGTTTGCGG  |
| 11 | 81 | 67 | GTCGGTACCGCAAAC  |

PSTI 22 (Segment I)
List fragments 1 to 11:

|    |    |    |                  |
|----|----|----|------------------|
| 1  | 7  | 1  | GAGAGTC          |
| 2  | 1  | 13 | GACTCTCTGGGTC    |
| 3  | 23 | 8  | TTAGCTTCACGACCCA |
| 4  | 14 | 30 | GTGAAGCTAAATGCTAC |
| 5  | 39 | 24 | CAGTTCGTTGTAGCAT |
| 6  | 31 | 47 | AACGAACTGAACGGTTG |
| •7 | 54 | 40 | GTAAGTGCAACCGTT  |
| •8 | 48 | 60 | CACTTACATCTAC    |
| 9  | 66 | 55 | CGGGTTGTAGAT     |
| 10 | 61 | 74 | AACCCGGTTTGCGG   |
| 11 | 81 | 67 | GTCGGTACCGCAAAC  |

PSTI 23 (Segment I)
List fragments 1 to 11:

|    |    |    |                  |
|----|----|----|------------------|
| 1  | 7  | 1  | GAGAGTC          |
| 2  | 1  | 13 | GACTCTCTGGGTC    |
| 3  | 23 | 8  | TTAGCTTCACGACCCA |
| 4  | 14 | 30 | GTGAAGCTAAATGCTAC |
| 5  | 39 | 24 | CAGTTCGTTGTAGCAT |
| 6  | 31 | 47 | AACGAACTGAACGGTTG |
| •7 | 54 | 40 | GAAAGTGCAACCGTT  |
| •8 | 48 | 60 | CACTTTCATCTAC    |
| 9  | 66 | 55 | CGGGTTGTAGAT     |
| 10 | 61 | 74 | AACCCGGTTTGCGG   |
| 11 | 81 | 67 | GTCGGTACCGCAAAC  |

PSTI 24 (Segment I)
List fragments 1 to 11:

|    |    |    |                  |
|----|----|----|------------------|
| 1  | 7  | 1  | GAGAGTC          |
| 2  | 1  | 13 | GACTCTCTGGGTC    |
| 3  | 23 | 8  | TTAGCTTCACGACCCA |
| 4  | 14 | 30 | GTGAAGCTAAATGCTAC |
| 5  | 39 | 24 | CAGTTCGTTGTAGCAT |
| 6  | 31 | 47 | AACGAACTGAACGGTTG |
| •7 | 54 | 40 | TTTAGTGCAACCGTT  |
| •8 | 48 | 60 | CACTAAAGAATAC    |
| •9 | 66 | 55 | CGGACGGTATTC     |
| •10 | 61 | 74 | CGTCCGGTTTGCGG  |
| 11 | 81 | 67 | GTCGGTACCGCAAAC  |

GENE CONSTRUCTIONS

The designed gene sequences were divided into oligonucleotide fragments (FIG. 1). These fragments have unique overlaps to allow a correct enzymatic assembly of DNA double strands in a multi-component reaction.

The basic strategy for the construction of PSTI gene variants involves the separate assembly of two segments of the genes:

Segment I from fragments 1 to 11, covering the variable amino acid positions 17 to 21

Segment II from fragments 12 to 25, covering the variable amino acid positions 29 and 32.

Table 3 shows the combinations of oligonucleotide fragments used to assemble the different segments I and II. Dots indicate fragments that differ from those of the master gene.

Enzymatic ligation of corresponding pairs of segments I and II will yield the desired complete gene variants. Gene multimers were first produced by allowing also blunt-end ligation at the 5'-termini of segments I and sticky-end ligation at the 3'-termini of segments II. Monomeric genes were excised from multimers by cutting with HincII and either HindIII, EcoRI or NcoI.

METHODS

Chemical Synthesis of Oligonucleotide Fragments

All necessary oligodeoxyribonucleotides were synthesized via established phosphotriester chemistry on cellulose disks as segmental supports (Frank et al., (1983), Nucleic Acids Res., 11, 4365–4377). They were purified by ion exchange HPLC on a Whatman Partisil SAX-10 column with a gradient of triethylammonium phosphate (pH 6.3) in 60% aqueous formamide.

Ligation of Oligonucleotides to Segment I and II DNA Duplices

Equimolar amounts (50 pmol) of each oligonucleotide fragment (see Table 3) were combined in siliconized plastic tubes (tube A: fragments comprising the upper strand; tube B: fragments comprising the lower strand). Fragments 1 and 11, as well as 12 and 25 that should not become phosphorylated (e.g., the ends of the duplices) were combined in a separate tube (tube C). The material was dried down. The oligonucleotides of tube A and B were phosphorylated at 37° C. for 30 minutes with a threefold excess of [$\gamma$-$^{32}$P]ATP (about 2 Ci/millimole) over 5'-hydroxyl termini in reaction mixtures of 10 $\mu$l containing 60 mM Tris.HCl (pH8), 6 mM MgCl$_2$, 10 mM DTE and 2 units of T4 PNK. After quantitative phosphorylation, T4 PNK was inactivated by heating tubes A and B to 95° C. for 2 minutes, and the contents were transferred to tube C. 10 mM DTE, 0.2 mM ATP and 2 units of T4 DNA ligase were added and the mixture was incubated at 40° C. for 1 hour. After cooling to 37° C. another 2 units of T4 DNA-ligase were added and incubation was continued at 37° C. for 1 hour, at 30° C. for 3 hours and at 15° C. overnight. Aliquots of the mixture were then analyzed by electrophoresis on a 0.04×20×40 cm, 10% nondenaturing polyacrylamide gel (acrylamide: methylenebisacrylamide-29:1, 50 mM Tris.borate (pH8.3), 1 mM EDTA) thermostated at 25° C. and run at 1000V until BPB had moved 25 cm. Samples for gel electrophoresis were loaded in a mixture containing 0.05% XC, 0.05% BPB, 10 mM EDTA and 4M urea and were not heated prior to loading. The original reaction mixtures were stored at $-20°$ C. until the result from gel electrophoresis indicated formation of a product of the expected length.

Then DNA ligase was inactivated by heating to 65° C. for 15 minutes. The ligation products were isolated from reaction mixtures by preparative gel electrophoresis on a 1 mm thick gel under conditions as above.

Assembly of Complete PSTI Gene Variants 10 pmol of corresponding segment I and II DNA were combined and phosphorylated at 37° C. for 30 min in a 20 $\mu$l reaction mixture containing 60 pmol [$\gamma$-$^{32}$P]ATP (200 Ci/mmol), 60 mM Tris.HCl (pH8), 6 mM MgCl$_2$, 10 mM DTE and 2 units of T4 PNK. Then 2 $\mu$l 1 mM ATP and 2 units of T4 DNA-ligase were added followed by incubation at 15° C. overnight. The reaction mixture was then diluted to 50 $\mu$l by adjusting to the proper buffer conditions for digestion with restriction enzymes.

For example PSTI gene variants
PSTI-1-Ala-32(-1A),
PSTI 3-Pro-32-(-3P),
PSTI 6-Ser-32 (-4A) and PSTI 5-Pro-32(5P)
were constructed following the above protocol.

Cloning of PSTI Variant Genes

Strategy

Genes are synthesized as described above starting from synthetic gene fragments with various sequences at the positions coding for amino acids 17, 18, 19, 20, 21, 29 and 32. The nomenclature PSTI-0 through PSTI-24 (see Table 1) refers to a particular coding sequence for the region of amino acids 17 to 21, followed by either A (for alanine), S (for serine), G (for glycine), or P (for proline) at position 32.

The gene constructions are planned so that variants in segment I can be recombined with variants in segment II (for example variants in pos. 32) after cleaving at a KpnI site at position 72-76 (FIG. 1).

Further variants are made by either site-specific mutagenesis on the gene fragments cloned in M13 mp-single strand bacteriophage vectors, using synthetic oligonucleotides, or as described previously by total gene synthesis.

Cloning

Genes for the PSTI-variants (for example PSTI-1A and PSTI-3P) having a flush end at the 5' terminus (amino terminal coding end) and a HindIII site at the 3' end were cloned into the HincII, HindIII restricted plasmid pUC8 (pUC-PSTI-1A and pUC-PSTI-3P).

PSTI variants containing an additional methionine at the NH$_2$-terminus (for example Met$^{-1}$-PSTI-4A) were cloned similarly into pUC8-NcoI (which contains the NcoI-linker CCCATGGG introduced in the HincII-site). pUC8-NcoI was restricted with NcoI, filled up with dNTP in the presence of DNA PolI (large fragment) and was further restricted with HindIII. By cloning of the gene for the PSTI-4A variant into this vector the NcoI restriction site is reconstituted (pUC-Met-PSTI-4A). Methods for restriction enzyme cleavage, ligation, transformation and screening for "insertional inactivation" of $\beta$ galactosidase activity are described in Maniatis, T., Fritsch, E. G., and Sambrook, J., Molecular Cloning, Cold Spring Harbor Publications, Cold Spring Harbor, 1982.

For further analysis and DNA-sequencing of some of the variants the HincII-HindIII PSTI-fragments were cloned into M13mp ($-$8, 9, 18 or 19) vectors according to the instructions of the manufacturer (Boehringer Mannheim).

The Preparation of Additional Variants Via Recombination

The restriction endonuclease KpnI cleaves in the PSTI gene of all constructions after base 76 on the upper strand and after base 72 on the lower strand producing 4 bp single stranded 3'-protruding ends (GTAC).

Following KpnI, ScaI double cleavage of pUC8-PSTI hybrids two fragments are obtained, containing in one fragment the 5' end of the gene with the variant sequences for amino acids residues 17 to 21 and in the other fragment the 3'-end of the gene with the variations in amino acids 29 and 32. Religation of fragments from different plasmids yields new recombinant pUC8-PSTI-variants with reassorted 5' and 3' regions (e.g. starting with PSTI-OP and PSTI-1A, one can derive PSTI-OA and PSTI-1P). The *Escherichia coli* K-12 strain RR1$\Delta$M15 and DH 1 were used as recipient hosts for the rearranged pUC8-PSTI variants (see ATCC 31343 and 33625).

The Preparation of Additional Variants Via Site Specific Mutagenesis

Starting material for this mutagenesis procedure are the M13 mp9-PSTI clones, made by cloning the HincII-HindIII PSTI-fragments from pUC8-PSTI variants into double stranded M13 mp9 bacteriophage according to the method of Messing, J and Viera, J (1982) *Gene,*

19, 269–276. Single strand hybrid bacteriophage was isolated and hybridised to a linear negative strand of the bacteriophage M13 mp9 rev. Synthetic oligonucleotides containing the sequence of the new variant at the site of mutagenesis are then hybridized to this so called "gapped duplex" and by the consecutive action of polymerase I (klenow fragment, Boehringer Mannheim) and DNA-ligase, filled in and ligated to form a closed circular double helix containing base mismatches at the site of mutagenesis. Transforming this DNA into mismatch-repair deficient *E. coli* MutS strain BMH 71-18 yields a high frequency of M13 mp9 rev-PSTI variants containing the new sequence determined by the synthetic "mutagenesis primer" which are selected subsequently in *E. Coli* su⁻ (amber suppressor-minus) strain MK 30-3. The experimental protocol follows that described by Kramer, W. et al., Nucl. Acids Res., 12, (1984). In this manner PSTI-8P, -9P, 10P, -11P, -12P, -15P, -17P, -18P and -19P were constructed.

DNA-Sequencing

DNA sequencing was carried out on single stranded M13mp8, M13mp9, M13mp18, M13mp9 (rev)-PSTI molecules using the dideoxy-method as described by Sanger, F. et al., (1977), Proc. Natn. Acad. Sci. U.S.A., 74, 5463-5467, or for pGV451 constructions according to the specific end-labelling and chemical degradation method of Volckaert G. et al., (1984), Gene Analysis Techniques, 1, 52-59.

Cloning in Expression Vectors

Production of PSTI-variant peptides was achieved by cloning into *E. coli* secretion vectors containing signal sequences of α-amylase (*B. subtilis*) or penicillin acylase (*E. coli*). The use of *E. coli* secretion vectors for the expression of a human secretory peptide like PSTI has the advantage that a fused signal peptide leads the gene product across the cytoplasmic membrane into the periplasmic space with concommitant processing of the signalpeptide (G. Kreil, (1981), Ann. Rev. Biochem., 50, 317-348) and release of active PSTI, either in its mature form or as a fusion product containing a linker peptide of a few amino acids at its aminoterminal end.

Methods for restriction enzyme cleavage: fill up of 5' protruding ends with dNTP in the presence of DNA pol I (large fragment), digestion with $S_1$ nuclease, gel electrophoresis of DNA, isolation of DNA fragments, ligation and transformation are described in T. Maniatis et al., Molecular Cloning, Cold Spring Harbor, (1982).

Construction of the α-amylase Secretion Vectors pCH 233 and pCH 2331

The α-amylase signal sequence from *B. subtilis* was derived from *Bacillus subtilis* DSM 704 (Deutsche Stammsammlung für Mikroorganismen, Göttingen) by cloning a partial Sau3A digest of chromosonal DNA into the BamH I site of pMK 3 (M. A. Sullivan et al., Gene (1984) 29, 21-26). One of the clones containing a 3 Kb DNA fragment with the α-amylase gene was modified by deletion of parts of the α-amylase structural gene in order to yield pALK1. DNA sequences of pALK1 revealed a possible ribosome binding site (RBS) and a signal sequence on a 230 bp EcoRI-BstEII fragment with extensive homology to an α-amylase from *B. subtilis* 1A289 (compare DNA sequence in FIG. 2 with M. Yandg et al., Nucleic Acid Research, (1983), 237-249). Since processing of the α-amylase signal sequence in *B. subtilis* was expected to occur at amino acid position 41 (see FIG. 2) fusion of the signal sequence to the PSTI reading frame was done at the BST EII-site. For this purpose we isolated from pALK1 an 230 bp fragment containing the possible Shine-Dalgano site and the signal sequence of α-amylase (fragment A in FIG. 3A). Fragment B containing the reading frame either for Met-PSTI-1A or Met-PSTI-4A was isolated from pUC-Met-PSTI-1A or pUC-Met-PSTI-4A (see "cloning of PSTI variant genes"). The ligation of the 3' flush end of fragment A to the 5' flush end of B fuses the reading frame of the α-amylase signal sequence to that of Met-PSTI-1A or (Met-PSTI-4A) thereby reconstituting the BstE II-and Nco I-restriction sites (FIG. 3B). The correct orientation of the A-B-fragment relative to the lac z promoter (see FIG. 3A) brings the gene for the PSTI-precursor under the control of lac $Z^{po}$ behind the reading frame of lac z' which should be terminated at the TAA-stop codon (pos. −58/−56 in the DNA sequence of fragment A, FIG. 2). Reinitiation of protein synthesis on the same mRNA should take place after binding of the ribosome to the possible Shine-Dalgano site of the α-amylase about 50 bases downstream from the stop codon at pos. −10 (see FIG. 2).

The PSTI-products from *E. coli* RR1ΔM15 transformed with pCH 233 (PSTI-1A) or pCH 2331 (PSTI-4A) revealed after protein purification and amino acid sequencing a fusion of 13 amino acids to the aminoterminus of the PSTI molecule (see examples 1 and 3). These additional amino acids starting with asn-ala-glu-thr ... were found to be identical to those in the α-amylase signal sequence starting from amino acid 32 in FIG. 3 B, indicating that processing of the PSTI-precursor by the *E. coli* signal peptidase takes place after the amino acid sequence ... pro-ala$_{29}$-ala-ala$_{31}$ ↓ in the signal sequence of bacillus α-amylase.

Construction of Penicillin Acylase Secretion Vectors pCH 2361, pCH 2362, and pCH 2363

Another signalsequence for the production of PSTI-variants was derived from *E. coli* penicillin acylase (PENAC), a periplasmic enzyme from *E. coli* ATCC 11105.

According to the DNA sequence of the penicillin acylase gene (W. Bruns et al., (1985), J. of Mol. and Appl. Genetics, 3, 36-44) a DNA fragment was synthesized containing the Shine-Dalgano site and signal sequence of PENAC which was modified by introducing an EcoR I site upstream and an EcoR V site downstream of the Shine-Dalgano site, a Bcl I-site at pos. 40 of the sequence in FIG. 4, thereby changing the amino acid 9 of the original PENAC signal sequence from valine to methionine. A Nhe I-site was introduced at the processing site of the PENAC signal sequence at amino acid 26. The PENAC-DNA fragment was assembled from 4 DNA fragments (pass 1-4, FIG. 4) as described for the PSTI genes and was cloned into pBR 322 restricted with EcoR I and Nhe I (pPENAC 1, FIG. 5A). Oligonucleotide synthesis of the DNA fragments pass 1-4 was done on an Applied Biosystems Model 380 DNA Synthesizer according to the manufacturer's instructions. The PENAC signal sequence was then moved under the control of lac $Z^{po}$ by cloning of the EcoRI-BamHI-fragment from pPENAC1 into pUC8 (pCH236 in FIG. 5A).

For the construction of the PENAC-expression-vector with the gene for PSTI-5P (pCH 2361) and for PSTI-3P (pCH 2362) pCH 236 was restricted and modified at the Nhe I-site (see FIG. 5A) and was further restricted with HindIII. Ligation of the gene for PSTI-5P (or for PSTI-3P) into the prepared pCH 236 fuses the PENAC signal sequence to the PSTI reading frame, resulting in the expression vector pCH 2361 (or pCH 2362). Again here as described above for pCH 233, the lac z' reading frame should terminate at the TAG-codon in front of the ShineDalgano site of PENAC (pos. 7-9 in FIG. 4).

For the production of Met-PSTI-4A (example 4) pCH 2363 was constructed by preparing pCH 236 similarly as described above. The gene for Met-PSTI-4A was isolated from pUC-Met-PSTI-4A (FIG. 5B).

Transformation of pCH 233, 2331, 2361, 2362 and 2363 Into E. coli RR1ΔM15 or DH$_1$ Standard procedures are used (T. Maniatis et al., 1982, Molecular Cloning—A Laboratory Manual; Cold Spring Harbor, N.Y.) for the transformation of competent E. coli DH 1 or RR1ΔM15 with pCH 233, 2331, 2361-2363, plating on selective media (agar plates with 50 μg/ml ampicillin), minipreparations and restriction analysis of plasmid DNA from single colonies. After screening for restriction sites present in the gene segment or in the expression vector the DNA sequence of the inserted DNA fragment was determined as described before for the synthetic genes.

Fermentation and Induction of E. coli RR1ΔM15 Transformed With pCH 233, 2331, 2361, 2362 and 2363

RR1ΔM15-transformed pCH 233, 2331, 2361, 2362 and 2363 were grown as overnight cultures. The medium contained 3% beef extract (Gibco), 1.5% yeast extract (Gibco) and 0.5% K$_2$HPO$_4$ in distilled water (pH 7.0) and 50 μg/ml Ampicillin. Care was taken to achieve a good aeration by incubation of the cultures in 1000 ml Erlenmeyer flasks filled with 100 ml medium.

The flasks were shaken on a Kühner RC-6-U at 28° or 37° C. at 190 rpm.

For the production of PSTI-variants overnight cultures were diluted 1:100 into fresh medium at 37° C. and grown for about 3 hours to optical densities of 1.5 A550 nm. Induction of the lac promoter was done by adding 1 mM isopropylthiogalactoside (Sigma) to the cultures. Fermentation was continued for 20 hours to about 4-6 A550 and cells were harvested by centrifugation at 8000 rpm (10′, 4° C. in a Kontron Centrikon H-401 with rotor A 6.14).

Isolation and Characterisation of the Inhibitors

Enzymes

Human leukocyte elastase (HLE) and porcine pancreas elastase (PPE) were obtained from Elastin Products Company, Inc. P.O. Box 147, Pacific, Miss. 63069/USA.

Bovine α-chymotrypsin (CHT) was obtained from E. Merck, Darmstadt.

Substrates

The substrates: MeOSuc-Ala-Ala-Pro-Val-pNA (HLE), Ac-Ala-Ala-Pro-Ala-pNA and Suc-Ala-Ala-Ala-pNA (PPE and Suc-Ala-Ala-Pro-Phe-pNA (CHT) were obtained from Bachem, Bubendorf/Switzerland.

Materials for Chromatography

Sephadex ® G-25; Sephadex ® G-50; Sepharose ® 4B-Cl, SP-Sephadex C-25 were obtained from Deutsche Pharmacia, Freiburg. The hydrophobic resin LGP 4429 is a product of Bayer AG, Leverkusen.

Methods

Chymotrypsin was immobilized onto Sepharose ® 4B-Cl after oxidation of the support with sodium periodate by reduction of the Schiff base formed with chymotrypsin with Na[CNBH$_3$] by the method of G. B. Roger et al., (1975), Biochem. Biophys.Res.Commun., 164, 478-484.

HPLC was performed with the use of appropriate columns. These are described in the text and/or the legendes to the corresponding figures.

Amino Acid Sequence Determination

About 0.5-2 nmol of the protein were dissolved in 30 μl TFA. The sample was applied to a glass fiber filter which was pretreated with 3 mg of polybrene. The sequence analysis was performed by the gas phase protein sequencer from APPLIED BIOSYSTEMS, Inc., USA according to Hewick (R. M. Hewick, M. W. Hunkapillar, L. E. Hood. W. Dreger, 1981, J. Biol. Chem. 256, 7990-7997). The amino acid phenylthiohydantoin derivatives liberated in each step were analysed using a cyano-HPLC column (DuPont) and a separation system described by Beyreuther (K. Beyreuther, B. Biesler, J. Bowens, R. Dildrop, K. Neufer, K. Stüber, S. Zais, R. Ehring, P. Zabel, 1983, Modern Methods in Protein Chemistry, p. 303-325, Walter de Gruyter + Co., Berlin). A WATERS HPLC system, including a M 510 pump, a WISP 710B autoinjector, a LC-spectrophotometer M 481, and a SHIMADZU integrator C-R3A, were used.

Acid Hydrolysis and Aminoacid Analysis

About 1 nmol of the protein is given in a pyrex tube to which 200 μl 6M HCl containing 0.05% 2-mercaptoethanol (I. T. Potts Jr., 1969, Anal. Biochem., 131, 1-15) was added. Tubes were sealed under vacuum and incubated at 110° C. for 22 hours. Hydrolysates were quickly dried, redissolved in 150 μl 0.2M sodium citrate buffer pH 2.2 and filtered. Amino acid analysis was carried out with a BIOTRONIC LC 5000 amino acid analyzer equipped with a fluorescence detector and a SHIMADZU C-R2AX integrator. Amino acids were quantified after reaction with o-phthaldialdehyde essentially as described by Benson (J. R. Benson, P. E. Hare, 1975, Proc. Natl. Acad. Sci., USA, 72, 619-622).

Enzyme Tests and Assays of Inhibitory Activities in Culture Filtrates

Culture filtrates were treated as follows: 10 μl TWEEN 80 solution (0.5%) and 50 μl perchloric acid (70%) were added to 1 ml of culture filtrate. After 20 min, these samples were centrifuged, and the clear supernatants were neutralized by the addition of 225 μl saturated solution of tris base. Aliquots of these solutions were taken to determine inhibitory activities.

Conditions of the enzyme assays are given in table 4. Generally, the samples were diluted with the appropriate buffer volume, and the enzyme was added. After the preincubation time, substrate was added (substrates are dissolved in DMSO in a concentration of 0.1M and diluted with buffer to give the concentration of the stock solution). The release of p-nitroaniline from the substrates was measured at 405 nm either continuously or after quenching the reaction by adding acetic acid. 100%- values were determined by running samples where inhibitors were omitted. Percentage inhibition was calculated using the formula:

$$\% \text{ inhibition} = 100 \times \left(1 - \frac{OD \text{ in the presence of inhibitor}}{OD \text{ in the absence of inhibitor}}\right)$$

Absolute amounts of inhibitors could be calculated by means of calibration curves, only after small amounts of purified substances became accessible.

The microorganisms of examples 3 and 6 of this application have been deposited with The National Collection Of Industrial Bacteria (NCIB), Torry Research Station, P.O. Box 31, 135 Abbey Road, Aberdeen AB9 8DG, Scotland, United Kingdom, under the designation NCIB 12365 and NCIB 12364 respectively.

EXAMPLE 1

Isolation of
$Asn^{-13}$-$Ala^{-12}$-$Glu^{-11}$-$Thr^{-10}$-$Ala^{-9}$-$His^{-8}$-$Lys^{-7}$-$Ser^{-6}$-$Asn^{-5}$-$Glu^{-4}$-$Val^{-3}$-$Thr^{-2}$-$Met^{-1}$-$Leu^{18}$-$Glu^{19}$-$Arg^{21}$-$Ala^{32}$-PSTI
(PSTI-4A[minifusion])

10 Liters of fermentation broth of RR1ΔM15/pCH 2331 were treated with 350 ml perchloric acid (70%). The precipitate was removed by centrifugation. The supernatant was neutralized with 8N KOH solution. The KClO₄ precipitate was removed by filtration using a Buchner-Funnel with suction after standing at 4° C.

The filtrate was passed over a gel bed of a chymotrypsin-Sepharose 4B-Cl conjugate at 4° C. (7×9 cm). The gel was washed with water until the optical density at 280 nm of the effluent reached zero. The gel was further washed with 500 ml 0.2M acetate buffer (pH 5) and 500 ml water. Finally, the gel was eluted with 0.2M acetic acid, adjusted to pH 2.0 with HCl. The elution profile is given in FIG. 6. Active fractions (as measured in the leukocyte elastase inhibition assay) were pooled, adjusted to pH 4 by the addition of solid sodium acetate, and concentrated by rotary evaporation. Salts and minor impurities were finally removed by preparative HPLC over a RP-318 column. The elution profile is given in FIG. 7. The purity of each fraction was checked by analytical HPLC. According to these results, three pools were made, tubes 42–44; 45–46 and 47–49, which yielded after lyophilization 6 mg, 12 mg, and 6 mg. Highest purity was achieved in the middle fraction, an analytical HPLC diagram of which is given in FIG. 8.

Data on amino acid composition, sequence analysis and inhibitory spectrum are given in Tables 5–7, hereinbelow.

EXAMPLE 2

Preparation of $Leu^{18}$-$Glu^{19}$-$Arg^{21}$-$Ala^{32}$-PSTI (PSTI-4A) from the minifusion protein by BrCN-cleavage 2.93 mg (0.46 μMol) of the PSTI-4A minifusion product (Example 1) were dissolved in 1 ml 70% formic acid. It was cleaved by adding 3 mg of cyanogen bromide and incubation for 18 h at room temperature under nitrogen atmosphere in the darkness. The reaction was stopped by diluting with 10 ml water. The water and the volatile by-products were removed by freeze drying. The $Leu^{18}$-$Glu^{19}$-$Arg^{21}$-$Ala^{32}$-PSTI (PSTI-4A) was separated from the side products and the uncleaved fusion protein by gelchromatography on a Sephadex ® G50 (superfine) column (2.5×90 cm) in 1% formic acid. The fractions were pooled according to their retention times on a Biorad RP-318 (4.6×250 mm) large pore column, solution A: 0.1% TFA; solution B: 0.1% TFA/60% acetonitrile flow 1 ml/minute, room temperature, detection at 210 nm; gradient: 0–60% B.

The fractions were lyophilized and purified by rechromatography on the same column using the same conditions. The active fractions were collected and lyophilized. The purity was checked by an analytical HPLC run of $Leu^{18}$-$Glu^{19}$-$Arg^{21}$-$Ala^{32}$-PSTI (PSTI-4A) as described in Example 1. The inhibitor was characterized by an amino acid analysis, N-terminal sequencing, HPLC and elastase inhibitory assay as depicted in Tables 5–7.

EXAMPLE 3

Isolation of
$Asn^{-13}$-$Ala^{-12}$-$Glu^{-11}$-$Thr^{-10}$-$Ala^{-9}$-$His^{-8}$-$Lys^{-7}$-$Ser^{-6}$-$Asn^{-5}$-$Glu^{-4}$-$Val^{-3}$-$Thr^{-2}$-$Met^{-1}$, $Leu^{18}$-$Ala^{32}$-PSTI (PSTI-1A[minifusion])

Four liters of fermentation broth of RR1ΔM15/pCH 233 were treated with 120 ml perchloric acid (70%), and a formed precipitate was removed by centrifugation (30 minutes, 4° C., 4000 rpm, Beckman J-6). The supernatant was adjusted to pH 8.6 with 8N NaOH solution, and passed over chymotrypsin-Sepharose 4B-Cl conjugate (8×10 cm). The gel was washed with 0.2M TRIS-HCl buffer (pH 8.6) until the optical density at 280 nm of the effluent reached the base line level. Next, the gel was eluted subsequently with water and 0.1M acetic acid, adjusted to pH 2 with HCl.

Fractions containing inhibitory activity (measured against leukocyte elastase) were pooled, adjusted to pH 2.7 with 8N NaOH-solution and applied to SP-Sephadex C-25 (2.5×35 cm) previously equilibrated with 0.15% trifluoroacetic acid (adjusted to pH 2.7 with NaOH solution).

After washing with the starting buffer, the column was developed with a linear gradient of NaCl from 0 to 1M in starting buffer. Fractions were pooled according to their inhibitory activity and to results of analytical HPLC runs (RP-318, BIO-RAD). The pool was concentrated by ultrafiltration over an UM2 membrane (Amicon), and the final purification was achieved by preparative HPLC chromatography over RP 318 (Gradient 0–60% Acetonitrile in 0.15% trifluoroacetic acid over 60 minutes). Two pools were formed and lyophilized, 8.7 mg of a homogeneous substance and 1.9 mg with minor impurities were obtained. Analytical data (amino acid analysis, sequence analysis and inhibitory activity) are given in tables 5–7.

Cyanogen bromide cleavage of the PSTI-1A minifusion protein was performed as described in example 2 and yielded $Leu^{18}$-$Ala^{32}$-PSTI (PSTI-1A)

EXAMPLE 4

Isolation of $Met^{-1}$-$Leu^{18}$-$Glu^{19}$-$Arg^{21}$-$Ala^{32}$-PSTI (Met-PSTI-4A)

One liter of fermentation broth of RR1ΔM15/pCH 2363 was treated with perchloric acid, centrifuged, and neutralized as described in Example 1 and finally passed over chymotrypsin-Sepharose 4B Cl conjugate (2.5×10 cm). The gel was washed with water, acetate buffer, and water as described in Example 1. Desorption of the inhibitor was brought forth by elution with 0.2M acetic acid, pH 2 (adjusted with HCl). Fractions containing the inhibitor were pooled. adjusted to pH 4 by addition of NaOH solution, and concentrated by rotary evaporation to 5 ml. Final purification was achieved by preparative HPLC on RP-318 using a gradient of 0 to 60% acetonitrile in 0.15% trifluoroacetic acid. Lyophilization of the pooled active fractions yielded 1.8 mg substance. Further data (amino acid composition, sequence analysis and inhibitory activity) are given in Tables 5-7.

EXAMPLE 5

Isolation of Tyr$^{18}$-Glu$^{19}$-Arg$^{21}$-PSTI (PSTI-3P)

750 ml fermentation broth of RR1ΔM15/pCH 2362 were treated with 25 ml perchloric acid and centrifuged after 30 min. The supernatant was neutralized by the addition of 4N KOH solution, and KClO$_4$ was removed by filtration after 6 hours. The filtrate was loaded onto a chymotrypsin-Sepharose-4B-Cl column (2.5×7 cm) which was subsequently washed with water and 0.2M acetic acid. The inhibitor was desorbed by means of 0.2M acetic acid, adjusted to pH 1.8 with HCl. Active fractions were pooled. adjusted to pH 3.5 with NaOH solution and concentrated by rotary evaporation. A slight precipitation was removed by centrifugation. and the supernatant was passed over RP-318 in a preparative HPLC. Freeze drying of the active fractions yielded about 0.8 mg inhibitor which was homogeneous in analytical HPLC. Analytical data (amino acid analysis, sequence analysis and inhibitory activity) are given in table 5-7.

EXAMPLE 6

Isolation of Val$^{18}$-Glu$^{19}$-Arg$^{21}$-PSTI (PSTI-5P)

To 3 liters of fermentation broth of RR1ΔM15/pCH 2361 100 ml of perchloric acid (70%) were added. After 30 minutes, the precipitate was filtered off, and the supernatant was brought to pH 7 with 8N NaOH solution. It was then passed over a hydrophobic resin (Lewapol LGP 4429, Bayer AG) previously washed with 0.1N HCl, methanol. and water (ϕ: 3 cm, bed height: 40 cm). The resin was washed with water and subsequently eluted with a linear gradient from 0 to 70% methanol. Inhibitory activity was determined in each fraction (leukocyte elastase inhibition assay after removal of methanol by evaporation). Active fractions were pooled and concentrated by evaporation in vacuo. The concentrate was acidified to pH 2.7 by addition of triflouroacetic acid and applied to SP Sephadex-G-25 (2.5×10 cm), which had been equilibrated with 0.15% triflouro acetic acid (pH 2.7, adjusted with NaOH).

The column was developed with a linear gradient of 0–1M NaCl in starting buffer. Inhibitory active fractions were pooled, neutralized, concentrated and desalted by means of filtration over Sephadex G-25 with 0.01M phosphate buffer, pH 7.0, as the eluent. The active fractions were adjusted to pH 2.7 and again chromatographed on SP-Sephadex-C 25 with a linear gradient of 0.1–0.5M NaCl at pH 2.7.

Figure 9:
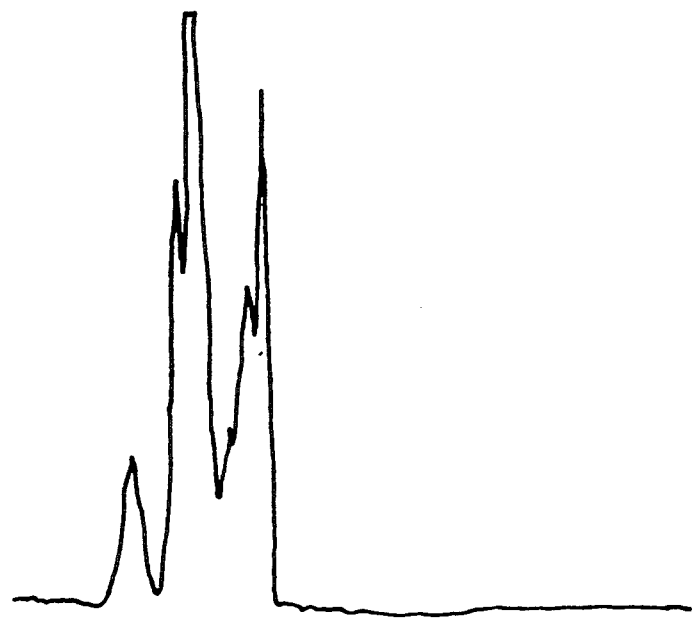
FIG. 9 is a plot depicting the final purification of PSTI-5P by HPLC.

The active eluates were adjusted to pH 4.0, concentrated, and further purified by passing them over RP-318 in a preparative HPLC. This step was once repeated. Final purification was achieved by preparative HPLC on an Mono-S-column from Pharmacia and subsequent rechromatography on RP-318 (FIG. 9). Analytical HPLC diagrams of the purified product are given in FIG. 10. Further analytical data (amino acid composition, sequence, inhibitory activities) are given in Tables 5-7.

TABLE 4

|  | Leukocyte Elastase (Human) | Pancreatic Elastase (Porcine) | α-Chymotrypsin (Bovine) |
|---|---|---|---|
| Buffer | 0.2M Tris. pH 8 + 0.1% TWEEN 80 | 0.2M Tris. pH 8 + 0.1% TWEEN 80 + 0.05% Na-Azid | 0.2M Tris. pH 8 + 0.05% TWEEN 80 |
| Total volume (after addition of substrate) | 0.65 ml | 0.65 ml | 0.60 ml |
| Amount of Enzyme per Assay | 50 ng | 25–50 ng | 50 ng |
| Preincubation Time | 30 minutes | 30–150 minutes | 30 minutes |
| Temperature | Room temp. | Room temp. | Room temp. |
| Substrate Formula | MeO—Suc—Ala—Ala—Pro—Val—pNA | Ac—Ala—Ala—Pro—Ala—pNA | Suc—Ala—Ala—Pro—Phe—pNA |
| Stock solution | 0.065M | 0.065M | 0.005M |
| Amount per Assay | 0.1 ml | 0.1 ml | 0.04 ml |
| Citation | 1) | 2) | 3) |
| Incubation temperature | 30° C. | 30° C. | room temp. |

1) Nakjima, K., Powers, J. C., Castillo, M. J., Ashe, B. M., Zimmerman, M., J. Biol. Chem. 254 (1979) 4027
2) Zimmerman. M., Ashe, B. M., Biochim. Biophys. Acta 480 (1977), 241
3) DelMar, E. G., Largman, C., Brodrick, J. W., Geokas, M. C., Anal. Biochem. 99 (1979) 316

TABLE 5

| | Amino acid analysis of several Inhibitors | | | | | | |
|---|---|---|---|---|---|---|---|
| Amino acid | PSTI-4A | PSTI-4A [mini-fusion] | PSTI-1A | PSTI-1A [minifusion] | Met-PSTI-4A | PSTI-5P | PSTI-3P |
| Asp | 6.45 (7) | 8.46 (9) | 8.09 (8) | 9.95 (10) | 6.91 (7) | 7.23 (7) | 6.70 (7) |
| Thr | 3.66 (4) | 5.48 (6) | 4.00 (4) | 5.50 (6) | 3.71 (4) | 3.67 (4) | 3.61 (4) |
| Ser | 2.83 (3) | 3.70 (4) | 2.79 (3) | 3.82 (4) | 3.24 (3) | 3.38 (3) | 2.47 (3) |
| Glu | 6.83 (7) | 9.45 (9) | 6.65 (6) | 8.61 (8) | 7.09 (7) | 7.79 (7) | 7.14 (7) |
| Gly | 4.91 (5) | 5.50 (5) | 5.37 (5) | 5.75 (5) | 5.52 (5) | 5.55 (5) | 4.94 (5) |
| Ala | 2.08 (2) | 3.70 (4) | 2.20 (2) | 4.0 (4) | 2.21 (2) | 1.19 (1) | 1.06 (1) |
| Val | 2.08 (2) | 3.02 (3) | 2.00 (2) | 3.19 (3) | 2.00 (2) | 2.83 (3) | 1.92 (2) |
| Met | — (0) | 0.88 (1) | — | 0.85 (1) | 1.14 (1) | — | — (0) |
| Ile | 1.80 (2) | 1.78 (2) | 2.73 (3) | 3.01 (3) | 1.86 (2) | 1.91 (2) | 1.70 (2) |
| Leu | 4.60 (5) | 3.13 (5) | 4.62 (5) | 5.03 (5) | 5.26 (5) | 4.00 (4) | 3.47 (4) |
| Tyr | 2.66 (3) | 3.13 (3) | 2.95 (3) | 2.65 (3) | 2.50 (3) | 3.01 (3) | 3.50 (4) |

TABLE 5-continued

| | | Amino acid analysis of several Inhibitors | | | | | |
|---|---|---|---|---|---|---|---|
| Amino acid | PSTI-4A | PSTI-4A [mini-fusion] | PSTI-1A | PSTI-1A [minifusion] | Met-PSTI-4A | PSTI-5P | PSTI-3P |
| Phe | 1.00 (1) | 1.14 (1) | 1.22 (1) | 1.25 (1) | 0.76 (1) | 1.35 (1) | 1.00 (1) |
| His | — (0) | 0.88 (1) | — | 1.15 (1) | — | — | — (0) |
| Lys | 2.91 (3) | 4.25 (4) | 2.84 (3) | 3.65 (4) | 3.42 (3) | 3.21 (3) | 2.67 (3) |
| Arg | 3.60 (4) | 4.11 (4) | 3.20 (3) | 3.22 (3) | 3.80 (4) | 4.22 (4) | 3.60 (4) |

The amino acids were measured after the post column derivatization with o-phthalaldehyde. Cys and Pro were not determined

TABLE 6

N-terminal acid sequence analysis of the PSTI-variants described in Table 5

| Derivative | Position | | | | | | | | | | |
|---|---|---|---|---|---|---|---|---|---|---|---|
| | 1 | 2 | 3 | 4 | 5 | 6 | 7 | 8 | 9 | 10 | 11 |
| PSTI-4A | Asp | Ser | Leu | Gly | Arg | Glu | Ala | Lys | Cys | Tyr | Asn |
| PSTI-4A minifusion | Asn | Ala | Glu | Thr | Ala | His | Lys | Ser | Asn | Glu | Val |
| PSTI-1A | Asp | Ser | Leu | Gly | Arg | Glu | Ala | Lys | Cys | Tyr | Asn |
| PSTI-1A minifusion | Asn | Ala | Glu | Thr | Ala | His | Lys | Ser | Asn | Glu | Val |
| Met⁻¹-PSTI-4A | Met | Asp | Ser | Leu | Gly | Arg | Glu | Ala | Lys | Cys | Tyr |
| PSTI-5P | Asp | Ser | Leu | Gly | Arg | Glu | Ala | Lys | Cys | Tyr | Asn |
| PSTI-3P | Asp | Ser | Leu | Gly | Arg | Glu | Ala | Lys | Cys | Tyr | Asn |
| | 12 | 13 | 14 | 15 | 16 | 17 | 18 | 19 | 20 | 21 | 22 |
| PSTI-4A | Glu | Leu | Asn | Gly | Cys | Thr | Leu | Glu | Tyr | Arg | Pro |
| PSTI-4A minifusion | Thr | Met | Asp | Ser | Leu | Gly | Arg | Glu | Ala | Lys | Cys |
| PSTI-1A | Glu | Leu | Asn | Gly | Cys | Thr | Leu | Ile | Thr | Asn | Pro |
| PSTI-1A minifusion | Thr | Met | Asp | Ser | Leu | Gly | Arg | Glu | Ala | Lys | Cys |
| Met⁻¹-PSTI-4A | Asn | Glu | Leu | Asn | Gly | Cys | Thr | Leu | Glu | Tyr | Arg |
| PSTI-5P | Glu | Leu | Asn | Gly | Cys | Thr | Val | Glu | Tyr | Arg | Pro |
| PSTI-3P | Glu | Leu | Asn | Gly | Cys | Thr | Tyr | Glu | Tyr | Arg | Pro |

TABLE 7

Inhibitory activities of PSTI variants according to the invention
The amounts of inhibitor giving 50% inhibition are presented

| Enzyme Inhibitor | α-Chymotrypsin (bovine) (50 ng/assay) | Granulocytic Elastase (human) (120 ng/assay) | Pancreatic Elastase (porcine) (500 ng/assay) |
|---|---|---|---|
| PSTI-4A [Minifusion] after Example 1 | 6 ng | 15 ng | 68 ng |
| PSTI-4A after Example 2 | 7 ng | 17 ng | 75 ng |
| PSTI-1A after Example 3 | 100 ng | 18 ng | 1200 ng |
| Met-PSTI-4A after Example 4 | 8 ng | 16 ng | 73 ng |
| PSTI-3P after Example 5 | 7 ng | >5000 ng | — |
| PSTI-5P after Example 6 | 100 ng | 15 ng | 70 ng |

DETAILED DESCRIPTION OF THE DRAWINGS

FIG. 1: Nucleotide and corresponding amino acid sequence of the PSTI master gene. Brackets and numbers indicate the synthetic oligonucleotides used to assemble the gene. The dashed line indicates the division of the gene into segment I (first part) and segment II (second part).

FIG. 2: DNA sequence of the 230 bp EcoRI-BstEII fragment from pALK1 containing the possible Shine Dalgano site (SD) around position −10 and the signal sequence from α-amylase (underlined amino acid sequence, starting at position 1). The possible processing site for the exoenzyme is indicated at amino acid 41 of the signal sequence.

FIG. 3A: Fragment A was isolated from pACK1 by cutting the plasmid with BstEII, and filled up with dNTP in the presence of DNApolI (large fragment). The DNA was phenolized, ethanol precipated and was further restricted with EcoRI. The 230 bp DNA fragment (A) was isolated after separation on a 2% agarose gel. The 180 bp fragment B was isolated similarly from pUC-Met-PSTI-1A (or from pUC-Met-PSTI-4A for the construction of pCH 2331) by restriction with NcoI, filled up with dNTP, ethanol precipitation, and further restriction with EcorRI. Both fragments A and B were ligated into an EcoRI restricted pUC8.

FIG. 3B: FIG. 3B shows the sequences at the junction between the α-amylase signal sequence (fragment A) and the Met-PSTI gene (fragment B) for either Met-PSTI-1A or -4A. The processing of the signal sequence in $E.\ coli$ takes place between amino acid 31 and 32 (see Example 1).

FIG. 4: FIG. 4 shows the synthetic EcoRI-NheI DNA fragment (PENAC) containing the possible Shine Dalgano site (around position 10) and the modified signal sequence of $E.\ coli$ penicillin acylase with the processing site at amino acid $Ala_{26}$.

FIG. 5: The synthetic PENAC-sequence (96 bp EcoRI-NheI fragment, compare FIG. 4) was cloned into pBR322, restricted with EcoRI and NheI in order to yield pPENAC1. pPENAC1 was restricted with EcoRI and BamHI, and the 250 bp DNA fragment containing a Shine Dalgano site and the PENAC signal sequence was ligated into pUC8 restricted with EcoRI and BamHI in order to yield pCH 236.

For the contruction of pCH 2361 (or pCH 2362) pCH 236 was restricted with Nhe I, and filled up with dCTP and dTTP in the presence of DNApolI (large fragment). The DNA was phenolized and ethanol precipitated and a S1 nuclease reaction was carried out in order to create a flush ended codon for Ala$_{26}$ at the cleavage site of the signal peptidase in the PENAC signal sequence (compare FIG. 4). After DNA precipitation pCH 236 was further restricted with HindIII and the vector was isolated after electrophoresis on a 0.8% agarose gel.

The gene for PSTI-5P was isolated by restriction of pUC-PSTI-SP with HincII and HindIII and the 180 bp fragment was isolated after electrophoresis on a 2% agarose gel. The gene for PSTI-30 was isolated similarly from pUC-PSTI-3P. Ligation of the 180 bp HincII-HindIII fragment from pUC-PSTI-5P (or pUC-PSTI-3 into pCH 236 yielded pCH 2361 (or pCH 2362).

Figure 5B:
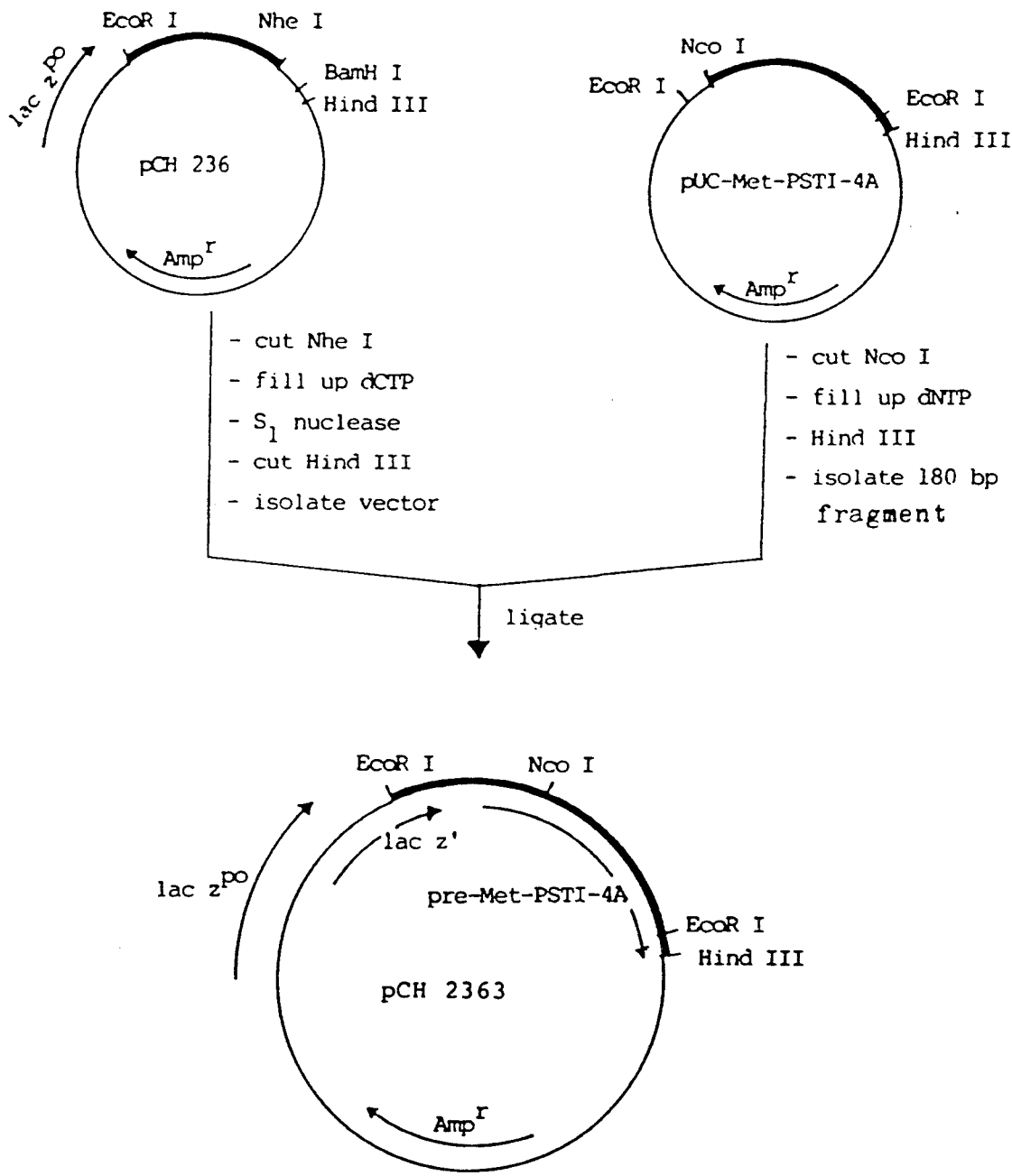
FIG. 5B depicts a schematic diagram for the construction of pCH 2363.

FIG. 5A: pCH 236 was restricted with NheI, and filled up with dCTP in the presence of DNApolI (large fragment). After DNA precipitation a S1 nuclease treatment was carried out in order to generate a flush end. The vector was further restricted with HindIII and isolate after electrophoresis on a 0.8% agarose gel. The gene for Met-PSTI-4A was isolated from pUC-Met-PSTI-4A by restriction with NcoI, and fill up with dNTP. After ethanol precipitation the DNA was further restricted with HindIII and the 180 bp fragment was isolated after electrophoresis on a 2% agarose gel.

Figure 6:
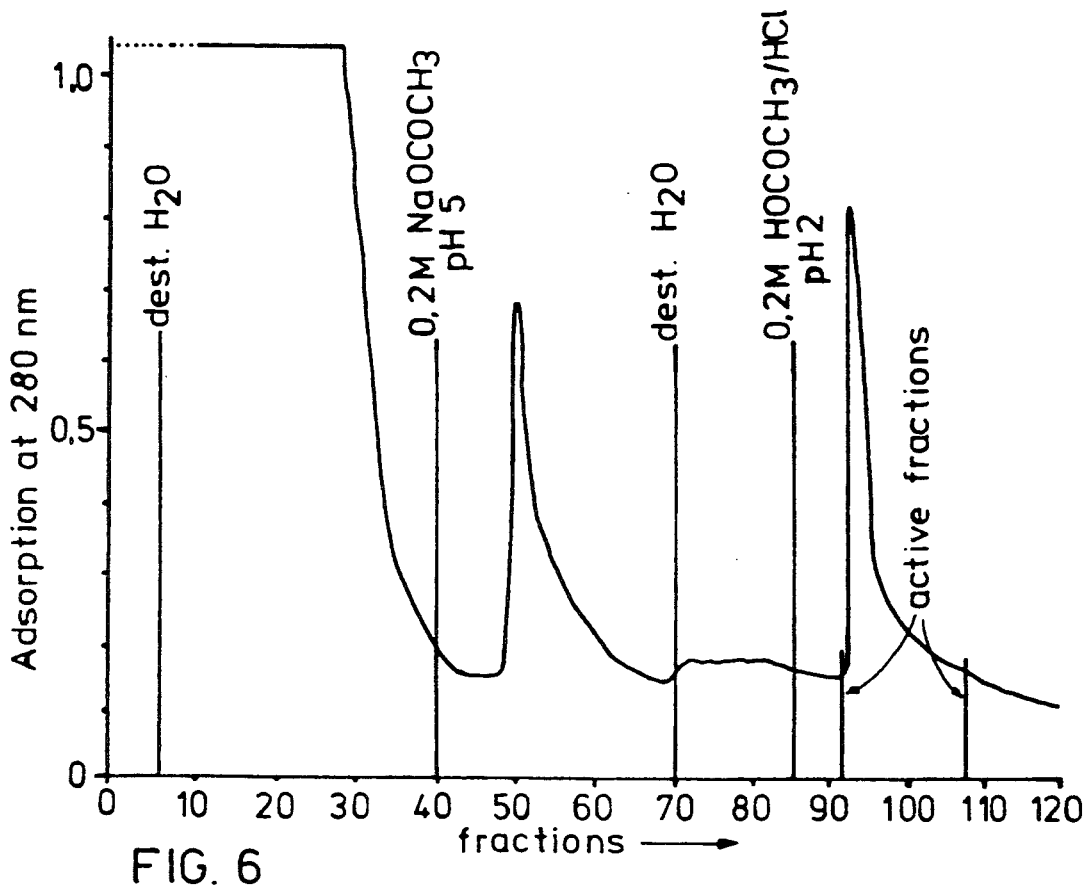
FIG. 6 is a plot depicting the results of the isolation of PSTI-4A by affinity chromatography.

FIG. 6: Isolation of PSTI-4A [minifusion] by affinity chromatography using a column (7×9 cm) with immobilized chymotrypsin at 4° C. Fractions of 11 ml were collected. On the abscissa the tube-No. are shown; on the ordinate the adsorption at 280 nm is given. The column was developed with water (to tube 40) followed by 0.2M acetate buffer pH 5.0 (to tube 70) destilled water (to tube 85). Final desorption was achieved with 0.2M acetic acid-hydrochloric acid of pH 2.0. The inhibitor was eluted in tubes 92-108.

Figure 7:
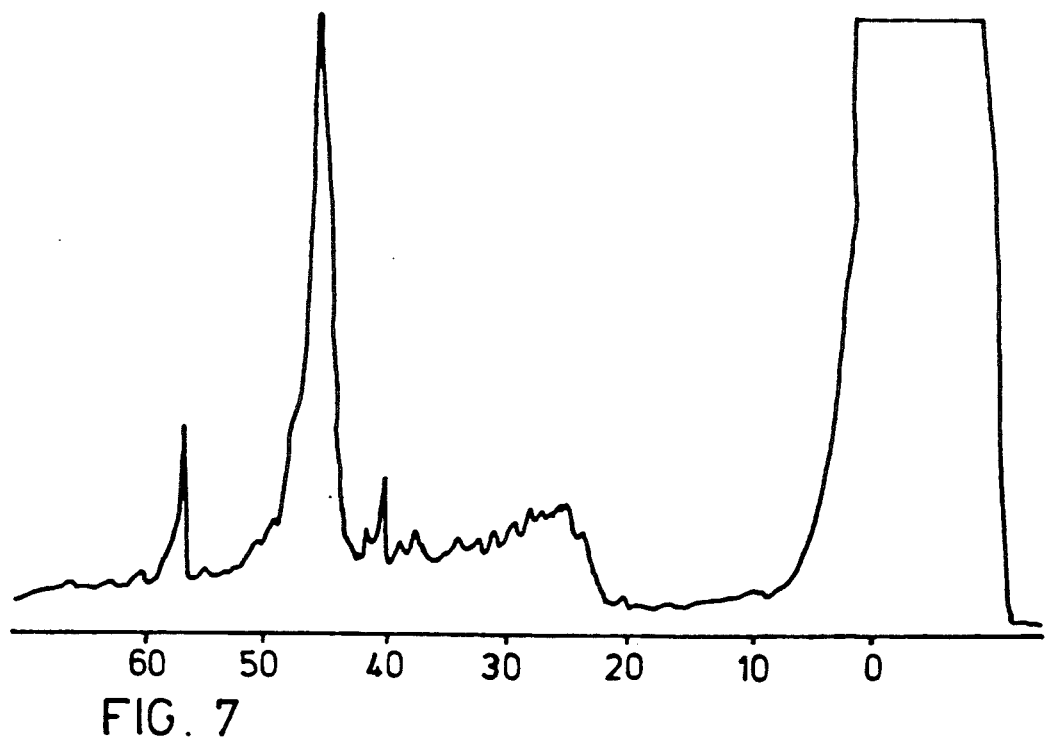
FIG. 7 is a plot depicting the results of HPLC of PSTI-4A.

FIG. 7: Preparative HPLC of the PSTI-4A [minifusion] containing eluates of the chymotrypsin-affinity column (tubes 92-108) on an RP-318-column (250-4.6 mm) (BIO-RAD). Elution was performed with a linear gradient of 0.15% trifluoroacetic acid and 60% acetonitrile containing 0.15% trifluoro acetic acid (2h). Flow: 1 ml/minute at 150 bar; detection at 220 nm. On the ordinate the adsorption at 220 nm is given, on the abscissa the tube-No. The inhibitor was eluted in tubes 44-50.

Figure 8:
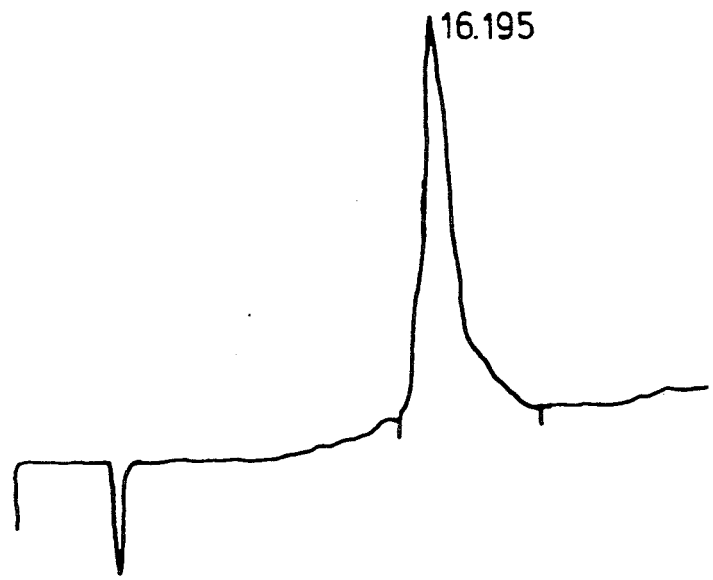
FIG. 8 is a plot depicting the results of HPLC of PSTI-4A.

FIG. 8: Analytical HPLC of PSTI-4A [minifusion] on an ultra-pak TSK SP-5 PW-column with precolumn (75×7.5 mm LKB).

| | Conditions: |
|---|---|
| Solvent A = | 0.15% trifluoro acetic acid and 0.1M Na$_2$SO$_4$, 10% methanol pH 2.7 |
| Solvent B = | 0.15% trifluoro acetic acid; 0.6M |

| | -continued |
|---|---|
| | Conditions: |
| Gradient: | Na$_2$SO$_4$, 10% methanol pH 2.7 |
| | 0-5 minutes 5% B |
| | 5-30 minutes 15-100% B |
| | 30-33 minutes 100-15% B |
| | 33-40 minutes 15% B |
| Flow: | 1.5 ml/minute at 20 bar |
| Detection: | 215 nm. |

FIG. 9: Final purification of PSTI-5P by preparative HPLC on RP-318 (250×4.6 mm) (BIO-RAD). Elution with a linear gradient of 0.15% trifluoro acetic acid and 0.15% trifluoro acetic acid, 60% acetonitrile in 2 hours. Flow: 1 ml/minute at 150 bar, detection at 280 nm. The inhibitor was eluted in tubes 20-27.

Figure 10:
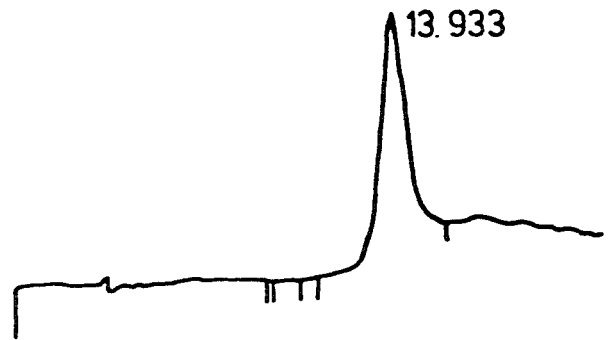
FIG. 10 is a plot depicting the results of an analytical HPLC of PSTI-5P.

FIG. 10: Analytical HPLC of PSTI-5P using a Bio-Sil® TSK CM-3-SW column (75×7.5 mm) (BIO-RAD) Conditions:

| | Conditions |
|---|---|
| Solvent A = | 0.15% trifluoro acetic acid, 10% methanol, 0.1M Na$_2$SO$_4$ |
| Solvent B = | 0.15% trifluoro acetic acid, 10% methanol 0.6M Na$_2$SO$_4$ |
| Gradient: | 0-5 minutes 15% B |
| | 5-30 minutes 15-100% B |
| | 30-32 minutes 100-15% B |
| | 32-40 minutes 15% B |
| Flow: | 1.5 ml/minute at 22 bar |
| Detection: | 215 nm |

It will be appreciated that the instant specification and claims are set forth by way of illustration and not limitation, and that various modifications and changes may be made without departing from the spirit and scope of the present invention.

What is claimed is:

1. A peptide having essentially the sequence of pancreatic secretory trypsin inhibitor selected from the group consisting of

| PSTI 1 | Thr-17 | Leu-18 | Ile-19 | Tyr-20 | Asn-21 | Asp-29 |
| PSTI 4 | Thr-17 | Leu-18 | Glu-19 | Tyr-20 | Arg-21 | Asp-29 |
| PSTI 5 | Thr-17 | Val-18 | Glu-19 | Tyr-20 | Arg-21 | Asp-29 |
| PSTI 6 | Thr-17 | Leu-18 | Glu-19 | Tyr-20 | Asn-21 | Asp-29 |
| PSTI 7 | Thr-17 | Leu-18 | Ile-19 | Tyr-20 | Arg-21 | Asp-29 |
| PSTI 11 | Pro-17 | Leu-18 | Glu-19 | Tyr-20 | Arg-21 | Asp-29 |
| PSTI 17 | Thr-17 | Val-18 | Ile-19 | Tyr-20 | Asn-21 | Asp-29 |
| PSTI 18 | Thr-17 | Ile-18 | Ile-19 | Tyr-20 | Asn-21 | Asp-29 |
| PSTI 21 | Thr-17 | Ile-18 | Glu-19 | Tyr-20 | Arg-21 | Asp-29 | further consisting in position 13 of Leu, in position 14 Glu, Asp or Asn, in position 32 Pro, Ser or Ala, and in position 36 Val.

2. A peptide according to claim 1, said peptide further consisting of methionine preceding Asp in position 1.

3. A pharmaceutical composition comprising an effective amount of the peptide according to claim 1 in admixture with a pharmaceutically acceptable diluent.

4. A unit dose of a composition according to claim 3 in the form of a tablet, capsule or ampule.

* * * * *

UNITED STATES PATENT AND TRADEMARK OFFICE
CERTIFICATE OF CORRECTION

PATENT NO. : 5,126,322

DATED : June 30, 1992

INVENTOR(S) : Collins et al.

It is certified that error appears in the above-identified patent and that said Letters Patent is hereby corrected as shown below:

Title Page     [54] Title:    Line 1 delete "TRYSPIN" and substitute
Col. 1, line 1                 -- TRYPSIN --

ABSTRACT:    Line 7 delete " inhibotory " and substitute
                             -- inhibitory --

Signed and Sealed this

Eighth Day of February, 1994

Attest:

BRUCE LEHMAN

*Attesting Officer*          *Commissioner of Patents and Trademarks*